United States Patent [19]

Verkade

[11] Patent Number: 5,344,948

[45] Date of Patent: Sep. 6, 1994

[54] SINGLE-SOURCE MOLECULAR ORGANIC CHEMICAL VAPOR DEPOSITION AGENTS AND USE

[75] Inventor: John G. Verkade, Ames, Iowa

[73] Assignee: Iowa State University Research Foundation, Inc., Ames, Iowa

[21] Appl. No.: 911,923

[22] Filed: Jul. 10, 1992

Related U.S. Application Data

[63] Continuation-in-part of Ser. No. 841,589, Feb. 25, 1992, abandoned.

[51] Int. Cl.$^5$ .............. C07F 7/00; C07F 7/02; C07F 9/02; C07F 5/00

[52] U.S. Cl. .............. 556/51; 556/1; 556/9; 556/14; 556/173; 556/174; 556/176; 556/181; 556/182; 556/186; 556/178; 556/136; 556/137; 556/138; 556/146; 556/81; 556/42; 556/45; 556/403; 568/1; 568/2; 568/6; 534/11; 534/15

[58] Field of Search ............ 568/1, 2, 6; 556/403, 556/1, 9, 14, 178, 174, 176, 181, 182, 186, 178, 136, 137, 138, 146, 51, 54, 81, 57, 45, 42; 534/11, 15

[56] References Cited

U.S. PATENT DOCUMENTS 5,051,533 9/1991 Verkade .............. 564/13

OTHER PUBLICATIONS

Voronkov et al., J. Organomet. Chem., vol. 233, pp. 1–147 (1982) (only pp. 102–107).
Cotton et al., Advanced Inorganic Chemistry, 4th Ed. Wiley-Interscience, New York (1980).
H. J. Cohen, J. Organometal. Chem., 5, 413–419 (1966).
B. de Ruiter et al., Inorg. Chem. 29, 1065–1068 (1990).
J. G. Verkade, Abstract of NSF Grant No. CHE-8908136.
M. G. Voronkov et al., J. Organometal. Chem., 233, 1–49 (1982).

(List continued on next page.)

Primary Examiner—Jose' G. Dees
Assistant Examiner—Porfirio Nazario
Attorney, Agent, or Firm—Schwegman, Lundberg & Woessner

[57] ABSTRACT

Neutral single-source molecular organic precursors containing tetradentate tripodal chelating ligands are provided that are useful for the preparation of films using chemical vapor deposition. These complexes can be generally represented by the formula

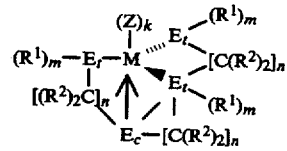

wherein "M" is selected from the group consisting of a lanthanide, an actinide, a Group IIIA metal, a Group IIIA metalloid, a Group IVA metal, a Group IVA metalloid, a Group VA metal, a Group VA metalloid, a Group IIIB metal, a Group IVB metal, a Group VB metal, a Group VIB metal, a Group VIIB metal, and a Group VIIIB metal. The ligand "Z" can be present or absent, i.e., $k=0-1$, and is selected from the group consisting of hydrogen, halide, and a group bonded to "M" through N, O, P, S, As, Si, or C. In the tetradentate tripodal chelating ligand "$E_c$" is N, P, or As, and $m=0-1$. When "$E_t$" is N, P, or As, $m=1$, and when "$E_t$" is O, S, or Se, $m=0$. Each "$R^1$" is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, a ($C_5$-$C_{18}$)heterocycle, and triorganosilyl. In —[C($R^2$)$_2$]$_n$—, $n=1$–4, and each "$R^2$" is independently selected from the group consisting of hydrogen, alkyl, alkenyl, alkynyl, aryl, aralkyl, and a heterocycle.

19 Claims, No Drawings

OTHER PUBLICATIONS

C. C. Amato et al., *Mat. Res. Soc. Symp. Proc.*, 168, 119–124 (1990).

D. A. Atwood et al., *J. Organomet. Chem.* 394, C6–8 (1990).

D. C. Bradley, *J. Chem. Soc.*, 3857–3861 (1960).

D. C. Bradley et al., *J. Cryst. Growth*, 75, 101–106 (1986).

T. A. Brooks et al., *Thin Solid Films*, 153, 521–529 (1987).

D. M-T. Chan et al., *Inorg. Chem.*, 25, 4170–4174 (1986).

H. L. M. Chang et al., *Mat. Res. Soc. Symp. Proc.*, 168, 343–348 (1990).

H. Cohen, *J. Organomet. Chem.*, 9, 177–179 (1967).

A. H. Cowley et al., *J. Am. Chem. Soc.*, 110, 6248–6249 (1988).

A. H. Cowley et al., *Angew. Chem. Int. Ed. Engl.*, 29, 1409–1410 (1990).

A. H. Cowley et al., *Chem. Mater.*, 2, 221–222 (1990).

A. H. Cowley et al., *Organometallics*, 10, 652–656 (1991).

A. H. Cowley et al., *Organometallics*, 10, 1635–1637 (1991).

A. G. Davies et al., *J. Organometal. Chem.*, 39, 279–288 (1972).

S. B. Desu et al., *Mat. Res. Soc. Symp. Proc.*, 168, 349–356 (1990).

D. D. Devore et al., *J. Am. Chem. Soc.*, 109, 7408–7416 (1987).

S. Dou et al., *Jiegou Huaxue*, 2, 273–276 (1983); *Chem. Abstr.*, 106, 129709z Abstract Only).

H. Du et al., *J. Am. Ceram. Soc.*, 73, 764–766 (1990).

C. Eaborn et al., *J. Chem. Soc. Chem. Commun.*, 317–318 (1976).

R. M. Fix et al., *J. Am. Chem. Soc.*, 112, 7833–7835 (1990).

R. M. Fix et al., *Chem. Mater.*, 2, 235–241 (1990).

H. Follner, *Acta Cryst.*, B28, 157–160 (1972).

R. J. Garant et al., *J. Am. Chem. Soc.*, 113, 5728–5735 (1991).

G. S. Girolami et al., *J. Am. Chem. Soc.*, 109, 1579–1580 (1987).

G. S. Girolami et al., *Mat. Res. Soc. Symp. Proc.*, 121, 429–438 (1988).

G. S. Girolami et al., *Mat. Res. Soc. Symp. Proc.*, 168, 319–329 (1990).

W. L. Gladfelter et al., *Mat. Res. Soc. Symp. Proc.*, 131, 447–452 (1989).

R. G. Gordon et al., *Chem. Mater.*, 2, 480–482 (1990).

R. G. Gordon et al., *J. Mater. Res.*, 6, 5–7 (1991).

D. Gudat et al., *Phosphorus, Sulfur and Silica*, 41, 21–29 (1989).

D. Gudat et al., *Organometallics*, 8, 2772–2779 (1989).

D. Gudat et al., *J. Am. Chem. Soc.*, 111, 8520–8522 (1989).

D. Gudat et al., *Organometallics*, 9, 1464–1470 (1990).

D. Gudat et al., *Organometallics*, 9, 2172–2175 (1990).

R. L. Harlow, *Acta Cryst.*, C39, 1344–1346 (1983).

D. E. Heaton et al., *Polyhedron*, 7, 1901–1908 (1988).

K.-L. Ho et al., *Mat. Res. Soc. Symp. Proc.*, 162, 605–610 (1990).

K.-L. Ho et al., *Proc. Electrochem. Soc.*, 90–12, 388–394 (1990).

M. G. Hocking et al., "Metallic and Ceramic Coatings", Longman Scientific and Technical: Essex, England, 1989, Ch. 4.

L. V. Interrante et al., *J. Electrochem. Soc.*, 136, 472–478 (1989).

K. Jones et al., *J. Chem. Soc.*, 1944–1951 (1965).

V. K. Jurkschat et al., *Z. anorg. allg. Chem.*, 463, 123–131 (1980).

N. Kakimoto et al., *Heterocycles*, 23, 1493–1501 (1985).

L. Korecz et al., *Inorg. Chim. Acta*, 58, 243–249 (1982).

M. A. H. Laramay et al., *J. Am. Chem. Soc.*, 112, 9421–9422 (1990).

M. A. H. Laramay et al., *Z. anorg. allg. Chem.*, 605, 163–174 (1991).

C. Lensink et al., *J. Am. Chem. Soc.*, 111, 3478–3479 (1989).

E. Liepins et al., *J. Organomet. Chem.*, 306, 327–335 (1986).

OTHER PUBLICATIONS

E. Lukevics et al., *Appl. Organomet. Chem.*, 2, 115–120 (1988).

E. Lukevits et al., *J. Gen. Chem. USSR*, 47, 98–101 (1977).

R. C. Mehrotra et al., *J. Indian Chem. Soc.*, 39, 677–682 (1962).

R. C. Mehrotra et al., *J. Indian Chem. Soc.*, 44, 467–472 (1967).

W. M. P. B. Menge et al., *Inorg. Chem.*, 30, 4628–4631 (1991).

J. E. Miller et al., *Chem. Mater.*, 2, 589–593 (1990).

W. T. Miller, *J. Am. Chem. Soc.*, 62, 2707–2709 (1940).

R. K. Mittal, *Z. anorg. allg. Chem.*, 351, 309–312 (1967).

A. A. Naiini et al., *Inorg. Chem.* 30, 5009–5012 (1991).

R. D. Peck et al., *J. Am. Chem. Soc.*, 81, 3984–3989 (1959).

J. Peive et al., *Dokl. Akad. Nauk SSSR*, 174, 986–8 (1967); *Chem Abstr.*, 67, 63364a (1967) (Abstract Only).

J. K. Ruff, *J. Am. Chem. Soc.*, 83, 2835–2839 (1961).

H. Schmidt et al., *Z. anorg. allg. Chem.*, 578, 75–80 (1989).

H. Schmidt et al., *Phosphorus, Sulfur and Silicon*, 49/50, 163–168 (1990).

E. E. Shestakov et al., *J. Gen. Chem. USSR*, 53, 1161–1166 (1983).

I. I. Solomennikova et al., *Latv. PSR Zinat. Akad. Vestis, Kim. Ser.*, 4, 491–493 (1975); Chem. Abstr., 83, 193248g (1975) (Abstract Only).

R. J. Speer, *J. Org. Chem*, 14, 655–659 (1949).

K. Starke, *J. Inorg. Nucl. Chem.*, 11, 77–79 (1959).

S. N. Tandura et al., *Topics in Current Chemistry*, 131, 99–189 (1986).

R. Taube et al., *Z. anorg. allg. Chem.* 581, 89–98 (1990).

A. Tzchach et al., *Z. anorg. allg. Chem.*, 413, 136–142 (1975).

W. G. Van Der Sluys et al., *Abstracts, 199th Meeting, ACS*, Boston, 1990, INOR 269.

M. G. Voronkov et al., *Khim. Geterotsikl. Soedin.*, 39–42 (1967); *Chem. Abstr.*, 67, 64321w (1967) (Abstract only).

J. Woning et al., *J. Am. Chem. Soc.*, 112, 4601 (1990).

J. Woning et al., *Organometallics*, 10, 2259–2266 (1991).

J. Woning et al., *J. Am. Chem. Soc.*, 113, 944–949 (1991).

S. K. Xi et al., *Inorg. Chem.*, 29, 2214–2220 (1990).

M. Zeldin et al., *J. Organometal. Chem.*, 86, 369–382 (1975).

SINGLE-SOURCE MOLECULAR ORGANIC CHEMICAL VAPOR DEPOSITION AGENTS AND USE

GOVERNMENT SUPPORT

The present invention was made with government support under Grant No. CHE-8908136 awarded by the National Science Foundation. The Government has certain rights in this invention.

CROSS REFERENCE TO RELATED APPLICATION

This application is a continuation-in-part of application Ser. No. 07/841,589, filed Feb. 25, 1992, now abandoned.

BACKGROUND OF THE INVENTION

Metallic and metalloid nitride, oxide, phosphide, sulfide, and arsenide films possess unique properties that make them useful coating materials for various applications. For example, nitride films can be used in applications where properties such as high temperature semiconduction, insulating thermal conduction, piezoelectric characteristics, thermal shock stability, and light emission capabilities are desired. Furthermore, nitride films can be used for device capping/protection, and in applications where extreme wear resistance for contacting surfaces is desired. Oxide films are often used to protect against corrosion and abrasion at high temperatures. Phosphide films can be used in applications that utilize the semiconduction properties they frequently display. Films containing mixed species, such as mixed oxide-nitride films, can also be used to protect against corrosion and abrasion at high temperatures.

Various techniques are used for the deposition of films such as these, including sputtering, plasma, and chemical vapor deposition ("CVD") techniques. For energy efficiency, convenience, and protection of the substrate material, it is desirable to carry out the deposition of films at as low a temperature as possible. Thus, conventional chemical vapor deposition techniques are the most desirable because they do not utilize such energy intensive physical processes as plasma enhancement and sputtering.

Chemical vapor deposition is a process "wherein a stable solid reaction product nucleates and grows on a substrate in an environment where a vapor phase chemical dissociation or chemical reaction occurs." M. G. Hocking et al., *Metallic and Ceramic Coating*, Longman Scientific and Technical: Essex, England, 1989, Chapter 4. In CVD, a heat-decomposable volatile precursor, such as an organometallic compound, is contacted with a substrate. The substrate is heated to a temperature required for decomposition of the precursor to the compound desired (typically, 200°-1500° C.). A coating thus forms on the substrate. Herein, such a decomposable volatile compound is referred to as a molecular organic chemical vapor deposition ("MOCVD") agent or precursor.

In addition to the low energy requirements of CVD techniques relative to plasma and sputtering techniques, CVD techniques are advantageous for forming films on substrates having an uneven surface or projections. Furthermore, with CVD techniques the compositions of the films can be more readily controlled. Also, films can be more readily prepared without contamination of, or damage to, the substrate using CVD techniques.

In the electronics industry, as well as other industries, there is a growing need for volatile precursors of various metals to be used in the chemical vapor deposition of metal nitride films, metal oxide films, and the like. An important characteristic of such metal precursors is the capability of evaporation or sublimation to give a metal-containing vapor or gas that can be decomposed in a controlled manner to deposit a film onto a target substrate. Relatively few organometallic complexes, however, are sufficiently volatile for use as MOCVD precursors.

Traditionally, metal nitride films have been deposited with CVD techniques using a separate molecular source for each of the elements in the product. Generally, the films consist of binary products, i.e., compounds containing only two types of elements. The components of the separate-source precursors typically include ligands such as hydrides, halides, and alkyls. Metal alkyls and hydrides can be quite toxic and/or flammable, however. Furthermore, the presence of a halogen atom in a film can promote corrosion. Thus, a need exists for more desirable MOCVD precursors.

To avoid some of the problems associated with separate-source MOCVD agents, single-source MOCVD agents are more desirable. Single-source precursors are compounds in which the elements of the product are incorporated into one starting material. They are desirable, for example, because the stoichiometry of the reactants can be more readily controlled than it can be with separate-source precursors. Also, the incorporation of impurities, such as carbon, into the deposited film can be more readily avoided using single-source precursors.

Single-source precursors can include Lewis acid-base donor-acceptor adducts wherein the Lewis base and the Lewis acid each contain one of the required elements for the product. The donor-acceptor adduct bonds, however, are usually not as robust as normal covalent bonds. Thus, dissociation occurs relatively easily upon heating and before volatilization with these adducts. As a result, the use of excess Lewis base is often required to produce quality films. Other currently used single-source materials are not generally stable in air, volatile at reasonable temperatures, or capable of producing reproducible films without impurities. Thus, a need exists for single-source chemical vapor deposition precursors that overcome the problems associated with the prior art separate-source and single-source materials.

SUMMARY OF THE INVENTION

The present invention is directed to a method for applying a film to the surface of a substrate by employing the techniques of chemical vapor deposition. The method involves the thermal decomposition of vapors comprising single-source molecular organic chemical vapor deposition ("MOCVD") agents or precursors. These single-source molecular organic, e.g., organometallic, precursors overcome many of the problems of separate-source precursors and many currently used single-source precursors. These precursors are useful for the deposition of films of metal and metalloid nitrides, phosphides, arsenides, and mixed species, such as oxide-nitrides, phosphide-nitrides, and the like.

The single-source molecular organic precursors of the present invention are neutral molecules that are of relatively low molecular weight such that they possess sufficient volatility to act as effective chemical vapor deposition agents. Preferably, the compounds of the present invention are volatile at a temperature below about 250° C. and a pressure below about 380 Torr. They are represented by the formula

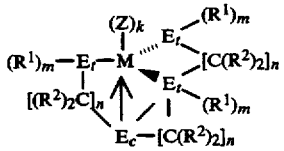

wherein k=0–1, m=0–1, and n=1–4. The central atom "M" is a metal or metalloid selected from the group consisting of a lanthanide, an actinide, a Group IIIA metal, a Group IIIA metalloid, a Group IVA metal, a Group IVA metalloid, a Group VA metal, a Group VA metalloid, a Group IIIB metal, a Group IVB metal, a Group VB metal, a Group VIB metal, a Group VIIB metal, and a Group VIIIB metal. Preferably, "M" is a metal or metalloid in Groups IIIA, IVA, IVB, VB, VIB, VIIB, or the Fe and Co group metals in VIIIB. For certain embodiments of the present invention, "M" is more preferably selected from the metals in Groups IVB, VB, VIB, VIIB, or the Fe group and Co group metals of Group VIIIB. For other embodiments of the present invention, "M" is more preferably a Group IVA metal or metalloid, a Group IVB metal, a Group VB metal, or a Group VIB metal.

Referring to the formula above, the ligand "Z" can be present or absent. That is, k can be 1 or 0. If "Z" is absent (k=0), "M" is preferably a metal or a metalloid selected from the group consisting of B, Al, Ga, In, Tl, Si, Ge, Sn, Ti, Zr, Hf, V, Nb, Ta, Cr, Mo, W, Mn, Tc, Re, Fe, Ru, Os, Co, Rh, and Ir; more preferably "M" is selected from the group consisting of B, Al, Ga, In, Tl, Si, Ge, and Sn; and most preferably "M" is B, Al, or Si. If "Z" is present (k=1), "M" is preferably a metal or a metalloid selected from the group consisting of Si, Ge, Sn, Ti, Zr, Hf, V, Nb, Ta, Cr, Mo, and W; more preferably "M" is Ti, Si, Ge, Sn, V, or Mo.

When "Z" is present (k=1), the ligand is selected from the group consisting of hydrogen, halide, and a ligand which bonds to central atom "M" through N, O, P, S, As, Si, or C. Preferably, "Z" represents a group bonded to central atom "M" through N, O, P, S, As, or Si. Of this group of ligands, "Z" is preferably a group bonded through N, O, S or Si. More preferably "Z" is a nitrogen-bound, sulfur-bound, or silicon-bound group. Most preferably, "Z" is a nitrogen-bound ligand. These ligands can be classified as either organic ligands if bound through a carbon atom, such as —CH$_3$, or inorganic ligands, such as —NCS or —SCN. Other ligands, such as —N(CH$_3$)$_2$ and —Si(CH$_3$)$_3$, may be classified as mixed inorganic/organic ligands.

The metal or metalloid in the molecule is complexed with a tetradentate tripodal chelating ligand in which "E$_c$" is N, P, or As, and each "E$_t$" is independently selected from the group consisting of N, P, As, O, S, and Se. Preferably each "E$_t$" is independently selected from the group consisting of N, P, As, and S. More preferably each "E$_t$" is independently selected from the group consisting of N, P, and As. Most preferably each "E$_t$" is N. When "E$_t$" is O, S, or Se, the "R$^1$" substituents are absent, i.e., m=0. When "E$_t$" is N, P, or As, m=1 and each "R$^1$" is independently selected from the group consisting of hydrogen, (C$_1$–C$_{20}$)alkyl, (C$_2$–C$_{20}$)alkenyl, (C$_2$–C$_{20}$)alkynyl, (C$_6$–C$_{18}$)aryl, (C$_7$–C$_{20}$)aralkyl, a (C$_5$–C$_{18}$)heterocycle, and triorganosilyl. The triorganosilyl groups are preferably of the formula —SiR$_3$ wherein each R is independently a (C$_1$–C$_4$)alkyl group.

In the tripodal ligand, the linking carbon chain, referred to in the above formula as —[C(R$^2$)$_2$]$_n$—, has a chain length 1 to 4 carbon atoms long, i.e., n=1–4. Preferably n=2–3, and more preferably n=2. Each "R$^2$" group in the linking carbon chain —[C(R$^2$)$_2$]$_n$— is independently selected from the group consisting of hydrogen, alkyl, alkenyl, alkynyl, aryl, aralkyl, and a heterocycle. More preferably, each "R$^2$" is independently selected from the group consisting of hydrogen, (C$_1$–C$_{20}$)alkyl, (C$_2$–C$_{20}$)alkenyl, (C$_2$–C$_{18}$)alkynyl, (C$_6$–C$_{18}$)aryl, (C$_7$–C$_{20}$)aralkyl, and a (C$_5$–C$_{18}$)heterocycle. When a vapor comprising a precursor is decomposed at the surface of a substrate, a film comprising a compound of the formula M$_x$E$_y$ is formed thereupon, wherein x=1–5, y=1–5 and E is N, P, As, S, O, Se, or mixtures thereof.

In the most preferred embodiments, all the atoms directly bonded to the metal or metalloid "M" are nitrogen atoms, i.e., "E$_t$"="E$_c$"=N, thereby forming "pnictides" or, more specifically "azametalatranes." Thus, the film deposited is a metal nitride M$_x$N$_y$ (wherein x and y are typically 1–5), preferably a binary metal nitride, such as TiN, Zr$_3$N$_4$, VN, Mo$_3$N$_4$, FeN, BN, AlN, GaN, InN, SiN, and the like.

In the context of the present invention, a "metalloid" is defined as an element whose properties are intermediate between those of a metal and those of a nonmetal. The elements that are typically considered to be metalloids are B, Si, Ge, As, Sb, Te, Po, and At. The metals referred to herein as lanthanides (La, Ce, Pt, Nd, etc.) and actinides (Ac, Th, Pa, U, Np, etc.) are those elements in the Periodic Table of the Elements with their outermost electrons in "f" orbitals.

The elements referred to herein by Group Numbers are the traditional classification numbers for the groups in the Periodic Table (not including the lanthanides and actinides). For example, Group IIIA metals/metalloids are B, Al, Ga, In, and Tl, which have also been referred to as the Group 13 elements according to the revised system recommended by the International Union of Pure and Applied Chemistry. The Group IVA metals/metalloids are Si, Ge, Sn, and Pb, which are referred to as Group 14 in this revised system. The Group VA metals/metalloids are As, Sb, and Bi, which are referred to as Group 15 in this revised system. The Group IIIB metals are Sc and Y (Group 3); the Group IVB metals are Ti, Zr, and Hf (Group 4); the Group VB metals are V, Nb, Ta, and Ha (Group 5); the Group VIB metals are Cr, Mo, and W (Group 6); the Group VIIB metals are Mn, Tc, and Re (Group 7); and the Group VIIIB metals are Fe, Ru, Os, Co, Rh, Ir, Ni, Pd, and Pt (Groups 8, 9, and 10).

Furthermore, in the context of the present invention, the term "alkyl" means a saturated linear, branched, or cyclic hydrocarbon group. The term "alkenyl" means an unsaturated linear, branched, or cyclic hydrocarbon group containing at least one carbon-carbon double bond, preferably 1–3 double bonds. The term "alkynyl" means an unsaturated linear, branched, or cyclic hydrocarbon group containing at least one carbon-carbon triple bond. The term "heterocycle" or "heterocyclic" means a mono- or polynuclear saturated or unsaturated cyclic group containing carbons and one or more, e.g., 1-4, heteroatoms such as nitrogen, non-peroxide oxygen, silicon, or sulfur or a combination thereof in the ring or rings. This includes heteroalkyl and heteroaryl cyclic systems. The term "aryl" means a mono- or polynuclear aromatic hydrocarbon group. The term "aralkyl" means a linear, branched, or cyclic alkyl hydrocarbon group having a mono-or polynuclear aromatic hydrocarbon or heterocyclic substituent, e.g., phenyl($C_1$–$C_4$)alkyl.

DETAILED DESCRIPTION OF THE INVENTION

The present invention provides a method for the deposition of metal and metalloid films and novel single-source molecular organic precursors for such deposition. The single-source molecular organic precursors of the present invention are neutral "cage" compounds wherein a central metal or metalloid is bound to a tetradentate tripodal chelating ligand. The tetradentate tripodal ligand occupies four coordination positions around the central metal or metalloid. A generalized representation of the precursors of the present invention is as follows, wherein a second ligand "Z" may be absent or present, i.e., k=0-1:

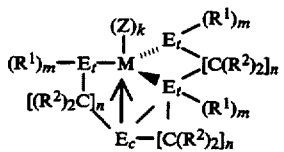

The compounds can be either monomeric or dimeric species. In the monomeric species, the central atom "M" is either four-coordinate, wherein the atom "M" is only bonded to the tetradentate ligand, or five-coordinate, wherein the atom is bonded to a second ligand in addition to the tetradentate ligand. Thus, in the monomeric four-coordinate structure, "Z" is not present (k=0), whereas in the monomeric five-coordinate structure, "Z" is present (k=1). The ligand "Z" is preferably a two-electron donor ligand, i.e., a ligand capable of donating two electrons to the central atom "M". It can be a monodentate ligand, or a bidentate ligand capable of bridging two molecules of the precursor or of expanding the coordination number of "M" to six.

It is to be understood that if the monomeric precursor is four-coordinate, a molecule of the compound may combine with a second molecule of the same compound, or a molecule of a different four-coordinate precursor complex of the present invention, and form a dimeric species. In such dimeric species, the central metal or metalloid is typically five-coordinate. The central core structure of such a dimeric species is as follows:

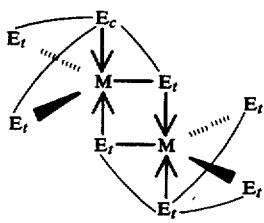

Furthermore, if the metal or metalloid of the monomeric precursor is five-coordinate, a molecule of the compound may combine with a second molecule of the compound, or with a molecule of a different five-coordinate precursor complex of the present invention, to form a dimeric species in which the central metal or metalloid is typically six-coordinate. The central core structure of such a dimeric species is as follows:

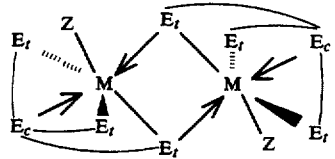

In these dimeric structural representations the representation of each of the two tetradentate tripodal ligands is simplified for ease of understanding. It is to be understood that each tripodal ligand is as defined in the generalized representation of the precursors of the present invention above. That is, each dimeric species includes two molecules of the precursor compounds of the present invention bound to each other through two $E_t$–M coordinate covalent bonds as indicated by the "$E_t \rightarrow M$" representation.

In the generalized representation above, the "M" atom can be a metal or metalloid in Groups III A and B, IV A and B, V A and B, VIB, VIIB, VIIIB, as well as the lanthanides and actinides. That is, "M" is selected from the group consisting of a lanthanide, an actinide, a Group IIIA metal, a Group IIIA metalloid, a Group IVA metal, a Group IVA metalloid, a Group VA metal, a Group VA metalloid, a Group IIIB metal, a Group IVB metal, a Group VB metal, a Group VIB metal, a Group VIIB metal, and a Group VIIIB metal. The "M" atom is preferably selected from the group consisting of a Group IIIA metal, a Group IIIA metalloid, a Group IVA metal, a Group IVA metalloid, a Group IVB metal, a Group VB metal, a Group VIB metal, a Group VIIB metal, a Group VIIIB iron group metal (Fe, Ru, Os), and a Group VIIIB cobalt group metal (Co, Rh, Ir).

For certain preferred embodiments of the present invention in which each "$E_t$" and "$E_c$" is a nitrogen atom, "M" is more preferably selected from the group consisting of a Group IVB metal, a Group VB metal, a Group VIB metal, a Group VIIB metal, a Group VIIIB iron group metal, and a Group VIIIB cobalt group metal. For other preferred embodiments of the present invention in which each "$E_t$" is N, P, As, O, S, or Se, "M" is more preferably selected from the group consisting of a Group IVA metal, a Group IVA metalloid, a Group IVB metal, a Group VB metal, and a Group VIB metal, and most preferably a metal in Groups IVB, VB, or VIB.

In preferred embodiments of the present invention, the central metal or metalloid "M" is in the +3 or +4 oxidation state. Furthermore, "M" typically achieves a higher coordination number than is required by its oxidation state. Thus, the presence (k=1) or absence (k=0) of the ligand "Z" can depend on the metal used. For certain embodiments, wherein k=0, the central "M" atom is preferably selected from the following list of metals or metalloids in Group IIIA, IVA, IVB, VB, VIB, VIIB, and VIIIB: B, Al, Ga, In, Tl, Si, Ge, Sn, Ti, Zr, Hf, V, Nb, Ta, Cr, Mo, W, Mn, Tc, Re, Fe, Ru, Os, Co, Rh, and Ir. More preferably, when k=0, "M" is selected from the following list of metals or metalloids in Groups IIIA and IVA: B, Al, Ga, In, Tl, Si, Ge, and Sn. Most preferably, when k=0, "M" is B, Al, or Si. For other embodiments, wherein k=1, the central "M" atom is preferably selected from the following list of metals or metalloids in Groups IVA, IVB, VB, and VIB: Si, Ge, Sn, Ti, Zr, Hf, V, Nb, Ta, Cr, Mo, and W. More preferably, when k=1, "M" is Ti, Si, Ge, Sn, V, or Mo.

The ligand "Z" can be hydrogen, halide (Cl, F, Br, I), or a donor group bonded to the central atom "M" through N, O, P, S, As, Si, or C. If the ligand is a group bonded through C, i.e., it is an organic group, it may be any of a variety of organic groups, such as alkanes, alkenes, alkynes, aryls, aralkyls, and species containing hetero atoms, such as N, S, O, and Si. Preferably, the carbon-bound ligand is selected from the group consisting of ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, and a ($C_5$-$C_{18}$)heterocycle. The ligands bound through N, O, P, S, As, or Si can be inorganic or organic ligands. That is, they can be classified as either organic ligands (e.g., —O(O)CMe and —SCH$_3$), inorganic ligands (e.g., =O and =N), or mixed organic/inorganic ligands (e.g., —Si(CH$_3$)$_3$ and —N(CH$_3$)$_2$).

The ligand "Z" is chosen such that it renders the precursor sufficiently volatile to be an effective MOCVD agent. Preferably, the ligand "Z" is chosen such that it renders the precursor volatile at a temperature below about 250° C., preferably below about 200° C., and at a pressure below about 380 Torr, preferably below about 250 Torr, and more preferably below about 10 Torr. Useable ligands include, but are not limited to, groups such as =O, =N, =N—t—Bu, —CH$_3$, —CH$_2$CH$_3$, i—Pr, —t—Bu, —NH$_2$, —N(CH$_3$)$_2$, —N$_3$, —NCS, —N(CH$_2$CH$_3$)$_2$, —O—t—Bu, —OPh, —O(O)CMe, —O—SiPh$_3$, —O—i—Pr, —C(O)Me$_2$Et, —C$_6$H$_5$, —SCH$_3$, —SCH$_2$CH$_3$, —SCN, —S—i—Pr, —S—CMe$_2$Et, —SPh, —S—CH$_2$CH=CH$_2$, —Si(CH$_3$)$_3$, —Si(CH$_2$CH$_3$)$_3$, —PPh$_2$, —PMe$_2$, —PPhMe, —AsPh$_2$, —AsMe$_2$, and —AsPhMe. Herein, "Ph" refers to a phenyl group, "Me" refers to a methyl group, "Et" refers to an ethyl group, "Pr" refers to a propyl group, and "Bu" refers to a butyl group.

Preferably, the precursors of the present invention contain donor ligands in the axial position, i.e., the position occupied by "Z", that do not render a carbide-contaminated film or a halide-contaminated film. Thus, the "Z" ligand is preferably a group bonded to, or capable of bonding to, the metal or metalloid "M" through N, O, P, S, As, or Si. Of this group of ligands, "Z" is an organic or inorganic nitrogen-bound group, oxygen-bound group, silicon-bound group, or sulfur-bound group, i.e., one which binds to the metal or metalloid "M" through the nitrogen, oxygen, silicon, or sulfur atom, respectively. More preferably, "Z" is an organic or inorganic sulfur-bound group, silicon-bound group, or nitrogen-bound group. Most preferably, "Z" is an organic or inorganic nitrogen-bound group. Of the nitrogen-bound ligands, "Z" is preferably —NCS, —NH$_2$, —N(CH$_3$)$_2$, and —N$_3$, more preferably —NH$_2$, —N(CH$_3$)$_2$, and —N$_3$, and most preferably —NH$_2$ and —N$_3$. Of the sulfur-bound ligands, "Z" is preferably —SCH$_3$, —SCH$_2$CH$_3$, —SCN, —S—i—Pr, —S—CMe$_2$Et, —SPh, and —S—CH$_2$CH=CH$_2$. Of the silicon-bound ligands, "Z" is preferably —Si(CH$_3$)$_3$ and —Si(CH$_2$CH$_3$)$_3$.

The tetradentate tripodal chelating ligand can be any of a variety of chelating structures with carbon chains —[C(R$^2$)$_2$]$_n$— between the chelating "E" atoms. The carbon chains are of a length that favors the formation of four bonds to the central atom "M" upon complexation. Although the "E$_t$" atoms at the ends of the three "arms" of the tripodal ligand will typically bond to "M" for a wide variety of lengths of the carbon connecting chain, e.g., wherein n=1–4, a useful chain length is one that favors the formation of a transannular bond between the central E$_c$ atom and "M" upon complexation. A transannular bond is an intramolecular donor-acceptor interaction between "E$_c$" and "M" whereby the lone pair of electrons on "E$_c$" are donated in a coordinate covalent fashion into a low lying vacant "p" or "d" orbital on the "M" atom. This transannular bond is represented in the above structure by the "E$_c$→M" bond.

Herein, there is a bond formed if the distance between two adjacent atoms is less than the sum of their van der Waals radii. Preferably, this requires that the carbon chains between "E$_c$" and each terminal "E$_t$" atom be 2 or 3 carbons long, i.e., n=2–3, and more preferably 2 carbons long, i.e., n=2. Thus, although the carbon chains between each "E$_t$" atom and the "E$_c$" atom can preferably be of the formula —C(R$^2$)$_2$—C(R$^2$)$_2$—C(R$^2$)$_2$— or —C(R$^2$)$_2$—C(R$^2$)$_2$—, or mixtures of these in one complex, it is more preferable if they are all of the formula —C(R$^2$)$_2$—C(R$^2$)$_2$—. The "R$^2$" groups in these carbon chains can be the same or different. They can be hydrogen or any of a variety of organic groups that render the precursors volatile at a temperature below about 250° C., preferably below about 200° C., and at a pressure of below about 380 Torr, preferably below about 250 Torr, and more preferably below about 10 Torr. This includes alkyls, alkenyls, alkynyls, aryls, aralkyls, heterocyclic groups, i.e., species containing hetero atoms, and mixtures thereof. As long as a transannular bond between "M" and the "E$_c$" atom is formed, the carbon atoms in the chain can also be a part of a cyclic system. For example, in —C(R$^2$)$_2$—C(R$^2$)$_2$— one "R" group on each —C(R$^2$)$_2$— moiety, taken together, can be —(CH$^2$)— wherein p is at least 1, and preferably p=1–4. Thus, for this example if the other "R$^2$" groups are H atoms, and if p=2, a linking group such as

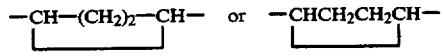

could be formed.

Preferably, each "R$^2$" group in the linking carbon chain —[C(R$^2$)$_2$]$_n$— is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, and a ($C_5$-$C_{18}$)heterocycle. Of these, each "R$^2$" is preferably selected from the group consisting of hydrogen and ($C_1$-$C_4$)alkyl groups. More preferably, each "R$^2$" is selected from the group consisting of hydrogen atoms and methyl groups, and most preferably they are all hydrogen atoms.

The central "E$_c$" atom in the tetradentate tripodal chelating ligand can be N, P, or As atoms, preferably it is N. This is advantageous because a transannular bond between "E$_c$" and "M" can form. The three "E$_t$" atoms in the trigonal plane of the chelated structure can independently be N, P, As, O, S, Se, preferably they are N, P, As, S. More preferably they are N, P, As, and most preferably they are each N. It is to be understood that the "$E_t$" atoms can be the same or different in any particular molecular organic precursor compound.

The substituents "$R^1$" attached to the "$E_t$" atoms may be the same or different, or they may be absent if "$E_t$" is O, S, or Se. Thus, m=0–1. That is, if "$E_t$" is O, S, or Se, m=0, whereas if "$E_t$" is N, P, or As, m=1. The substituent "$R^1$" can include alkanes, alkenes, alkynes, aryls, arylalkyls, and species containing hetero atoms, such as N, S, O, and Si. Thus, the substituents "$R^1$" can be selected from the group consisting of hydrogen, ($C_1$–$C_{20}$)alkyl, ($C_2$–$C_{20}$)alkenyl, ($C_2$–$C_{20}$)alkynyl, ($C_6$–$C_{18}$)aryl, ($C_7$–$C_{20}$)aralkyl, a ($C_5$–$C_{18}$)heterocycle, and triorganosilyl. The triorganosilyl groups are preferably of the formula —$SiR_3$, wherein each R is independently a ($C_1$–$C_4$)alkyl group. Preferably, "$R^1$" is selected from the group consisting of hydrogen, ($C_1$–$C_4$)alkyl groups, and triorganosilyl groups of the formula —$SiR_3$ wherein each R is independently a ($C_1$–$C_4$)alkyl. More preferably, each "$R^1$" is selected from the group consisting of hydrogen, methyl groups, and —$SiMe_3$ groups. Most preferably, each "$R^1$" substituent is a hydrogen atom.

Referring to the generalized representation of the molecules of the present invention, for certain preferred embodiments of the present invention when "M" is Ti and k=1, "Z" is preferably: an —$OR^3$ group wherein $R^3$=k=1, ($C_4$–$C_{10}$)alkyl, ($C_6$–$C_{18}$)aryl, ($C_7$–$C_{20}$)aralkyl, and —$C(O)R^4$ wherein $R^4$=($C_1$–$C_4$)alkyl; an —$N(R^5)_2$ group wherein $R^5$=H or ($C_1$–$C_4$)alkyl; or an —$SR^6$ group wherein $R^6$=($C_1$–$C_{10}$)alkyl, ($C_2$–$C_{10}$)alkenyl, ($C_6$–$C_{18}$)aryl, and ($C_7$–$C_{20}$)aralkyl. For these titanium complexes $E_c$ is N; each $E_t$ is O; m=0; n=1–4; and each "$R^2$" in —[$C(R^2)_2$]$_n$— is independently selected from the group consisting of hydrogen, ($C_1$–$C_{20}$)alkyl, ($C_2$–$C_{20}$)alkenyl, ($C_2$–$C_{20}$)alkynyl, ($C_6$–$C_{18}$)aryl, ($C_7$–$C_{20}$)aralkyl, and a ($C_5$–$C_{18}$)heterocycle. Titanium complexes such as these can be monomeric or dimeric.

For other preferred embodiments of the present invention, when "M" is V, "M—Z" is preferably the vanadium oxide group "V=O" or a vanadium amide group V=$NR^7$, wherein $R^7$ is selected from the group consisting of ($C_1$–$C_4$)alkyl and triorgansilyl groups. Preferably $R^7$ is a triorganosilyl of the formula —$SiR_3$ wherein each R is a ($C_1$–$C_4$)alkyl. Furthermore, when "M" is Mo, "M—Z" is preferably the molybdenum nitride group "Mo≡N".

For certain other preferred embodiments of the present invention, when "M" is Ge or Sn, k=0–1, and $E_c$ and each $E_t$ are N (m=1), "Z" is selected from the group consisting of hydrogen, halide, and a ligand which bonds to M through N, O, P, S, As, Si, or C. Each "$R^2$" in —[$C(R^2)_2$]$_n$— is independently selected from the group consisting of hydrogen, ($C_1$–$C_{20}$)alkyl, ($C_2$–$C_{20}$)alkenyl, ($C_2$–$C_{20}$)alkynyl, ($C_6$–$C_{18}$)aryl, ($C_7$–$C_{20}$)aralkyl, and a ($C_5$–$C_{18}$)heterocycle. Each "$R^1$" is selected from the group consisting of hydrogen, ($C_1$–$C_{20}$)alkyl, ($C_2$–$C_{20}$)alkenyl, ($C_2$–$C_{20}$)alkynyl, ($C_6$–$C_{18}$)aryl, ($C_7$–$C_{20}$)aralkyl, a ($C_5$–$C_{18}$)heterocycle, and triorganosilyl.

Because of the augmentation in coordination number in these chelated structures, numerous advantages are realized with the use of this class of compounds as single-source MOCVD agents. For example, metal or metalloid "M" is protected from nucleophilic attack by adventitious water or oxygen. Thus, these compounds are generally relatively stable to handling in air. Furthermore, these compounds are generally volatile at reasonable temperatures under vacuum. Thus, ligands are chosen such they render the precursors volatile at a temperature below about 250° C., preferably below about 200° C., and a pressure below about 380 Torr, preferably below about 250 Torr, and more preferably below about 10 Torr. The molecular weights of these compounds are typically less than about 800 g/mole, preferably less than about 500 g/mole, and more preferably less than about 300 g/mole.

Preferred Single-Source Precursors

Metal alkoxides and their amide analogs, particularly those that are highly symmetrical, are of particular interest as CVD precursors to new materials, such as metal oxide and metal nitride films. This is generally because of their volatility. Preferred single-source precursors of the present invention useful for the synthesis of metallic and metalloid films, particularly nitrides, phosphides, arsenides, oxides, and oxide-nitrides, are based on chelated structures A and B shown below.

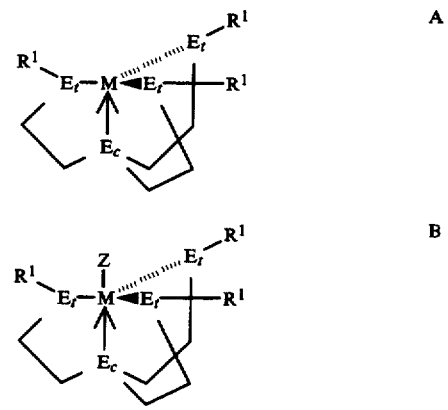

In both structures A and B, the preferred linking chain between the "E" atoms is a —$CH_2$–$CH_2$— moiety; and "$R^1$", if it is present, is preferably selected from the group consisting of hydrogen, ($C_1$–$C_4$)alkyl groups, and triorganosilyl groups of the formula —$SiR_3$ wherein each R is a ($C_1$–$C_4$)alkyl group. As discussed above, in both structures A and B the central metal or metalloid "M" typically achieves a higher coordination number than is required by its oxidation state. Herein, molecules of both types A and B are referred to as metalatranes, although the term "atrane" has traditionally been reserved for five-coordinate complexes of type B. If all the "$E_t$" and "$E_c$" atoms are nitrogen atoms, i.e., "$E_t$"="$E_c$"=N, the complexes are referred to as azametalatranes. Preferred examples of metalatranes and azametalatranes, wherein "M" is selected from the metals and metalloids of Groups IIIA, IVA, IVB, VB, and VIB, are set forth in the Experimental Section for Ti, Si, Ge, Al, B, Sn, V, and Mo.

For the preparation of nitride films all the "$E_t$" and "$E_c$" atoms are preferably nitrogen atoms. Analogously, for phosphide films all the "$E_t$" and "$E_c$" atoms are preferably phosphorus atoms, and for arsenide films all the "$E_t$" and "$E_c$" atoms are preferably arsenic atoms. For mixed oxide-nitride films "$E_c$" is a nitrogen atom, and the "$E_t$" atoms are nitrogen or oxygen atoms, with at least one "$E_t$" atom being a nitrogen and at least one "$E_t$" atom being an oxygen. Because it is advantageous for the compounds of the present invention to have a transannular "$E_c \rightarrow M$" bond, it would be very difficult to force "$E_c$" to be an oxygen atom, which would be desirable for the preparation of oxide films. It is believed, however, that oxide films can be prepared from complexes of the present invention if all other atoms directly bonded to the central atom "M" are oxygen atoms. As discussed above, if the "$E_t$" atoms are oxygen atoms, the "$R^1$" groups are absent.

For the chelated structures of type A, it is also possible to produce a dimeric structure. For example, if "M"=Al, and each "E"=N, the following structure is possible, in which aluminum displays its not uncommon five-coordinate nature.

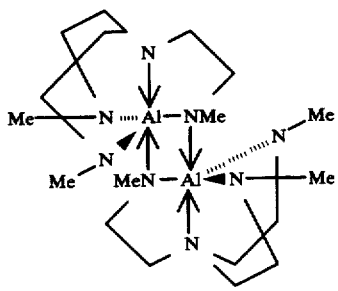

Similarly, for the chelated structures of type B, it is possible to produce a dimeric structure. For example, if "M"=Ti and each "E"=O, the following structure is possible, in which titanium displays its not uncommon six-coordinate nature.

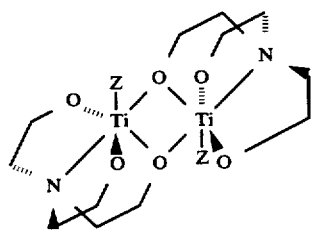

Alternatively, a dimeric structure with the molecules combined through a bridging oxygen atom could arise from partial hydrolysis or thermal decomposition. For example, if "M"=Ti and each "E"=N, the following structure is possible.

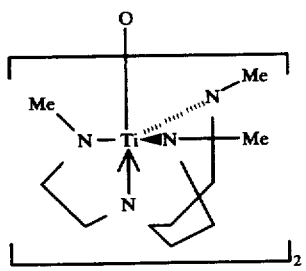

Preferred compounds with the structures A and B are generally volatile at reasonable temperatures, e.g., less than about 250° C., under vacuum. Because dimeric species arise by adduction of two molecules of type A or B, these dimers are generally also volatile. That is, if the precursors dimerize to structures similar to those shown above, this is not necessarily deleterious. Compounds such as these may be sufficiently volatile owing to the lack of a net molecular dipole moment in their centrosymmetric structures, or they may dissociate into monomers upon heating. Thus, dimeric compounds of molecules of type A or B are useable as molecular organic chemical vapor deposition agents.

Because of the possibility of dimerization, heterobimetallic dimers of compounds of type A can be prepared. For example, by equilibrating pairs of compounds such as

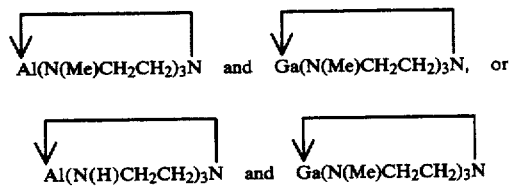

in solution, Al-Ga dimers of type A can be formed. Heterobimetallic dimer formation is generally favored over homometallic dimer formation because the donor bonds coupling the monomers are typically strengthened in going from a homometallic dimer to a heterobimetallic dimer. This is believed to occur because the lighter-metal monomeric component will be more Lewis acidic, and the nitrogen of the heavier-metal monomeric component will be more electron rich (owing to the lower Lewis acidity of the heavier metal). Thus, alloy compositions can be formed by volatilizing heterobimetallic dimeric compounds.

It is also to be understood, however, that alloy compositions can be formed by simultaneously volatilizing two different compounds of type A or type B, whether monomeric or dimeric. Furthermore, layering of films can be accomplished by sequential volatilization of compounds of type A or type B, whether monomeric or dimeric.

Compounds of structures A and B feature a high ratio of E/M, which is often found to favor film formation of the binary compound "ME" in the separate-source precursor approach. Thus, addition of an $EH_3$ gas, such as $NH_3$ for the formation of metal nitrides, is typically not necessary to attain stoichiometry with the precursors of the present invention, although a gas can be added if desired. The utilization of pure precursors of types A and B, without added gases, typically insures better reproducibility of film properties.

Methods of Preparation

Typical reaction sequences for the preparation of the single-source precursors of types A and B are as follows:

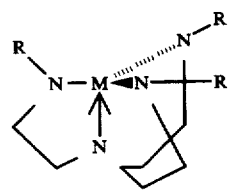

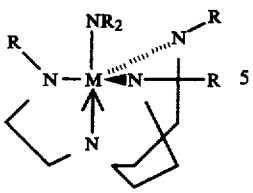

Similar reaction sequences are used for the preparation of metalatranes using triethanolamine and metal alkoxides. The driving force for these reactions is entropically favored chelation, which typically provides stable and easily manipulated products. Although the stability of the trivalent oxidation state decreases with elements lower in a specific group, such as from Ga to In for example, their compounds generally gain considerable stability from complexation through the extensive chelation of the metal favored by the preferred three five-membered rings. By the straightforward reaction of Ti(NMe$_2$)$_4$, for example, with (MeHNCH$_2$CH$_2$)$_3$N, the TiN precursor

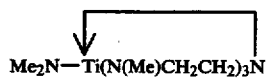
Me$_2$N—Ti(N(Me)CH$_2$CH$_2$)$_3$N is formed as a volatile red liquid.

Five-coordinate compounds of type B with various ligands in the axial position, i.e., as a "Z" group, can be readily synthesized by substitution reactions. For example,

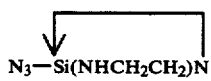
N$_3$—Si(NHCH$_2$CH$_2$)N can be synthesized as follows:

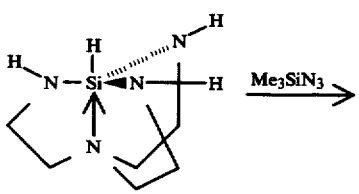

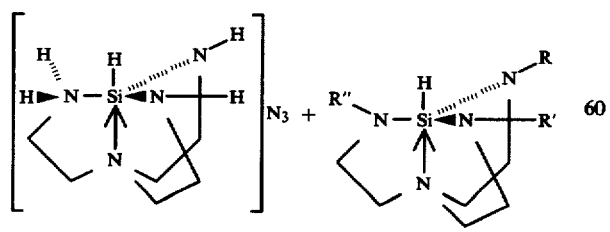

R = SiMe$_3$, R' = H, R" = H
R = R' = SiMe$_3$, R" = H
R = R' = R" = SiMe$_3$

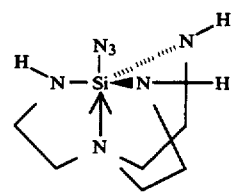

Type B compounds in which "Z" is an alkoxy group can be readily synthesized. For example, using (dimethylamino)titanatrane

(Me$_2$N—Ti(OCH$_2$CH$_2$)$_3$N), analogous complexes with "Z"=OR$^3$, wherein R$^3$ is as defined above, can be prepared in better than 90% yield. Under the mild conditions of the reaction, the pathway for displacement is believed to involve nucleophilic attack of an alcoholic oxygen on the metal to form a six-coordinate intermediate followed by cleavage of the thermodynamically less stable Ti-NMe$_2$ bond and elimination of Me$_2$NH. This complex (R$^3$O—Ti(OCH$_2$CH$_2$)$_3$N)

can exist at room temperature in a dimeric form, or a monomeric form in complexes in which there are bulky monodentate substituents on the metal. (Dimethylamino)titanatrane also reacts with thiols giving the indicated yellow or orange thiolatotitanatrane dimers, in which "Z"=SR$^6$, wherein R$^6$ is as defined above, in better than 85% yield in most cases.

Monomeric versions of some of the dimeric systems herein described are favored by incorporating sufficiently bulky groups attached to the nitrogen "E$_t$" atoms. A preferred group is —SiMe$_3$ for two reasons. First, N—Si bonds are comparatively weaker than N—H or N—C bonds, allowing them to more easily thermally decompose, thereby providing the central metal with maximum access to the nitrogen. Second, the synthesis of such compounds is generally quite simple. The following example represents a method of introducing Me$_3$Si groups:

MeSi(NMe$_2$)$_3$ + (H$_2$NCH$_2$CH$_2$)$_3$N ⟶

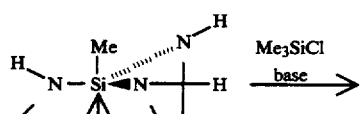

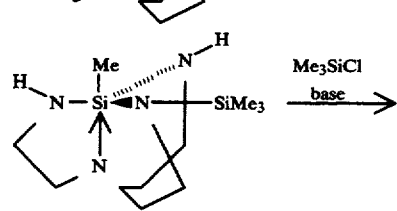

-continued

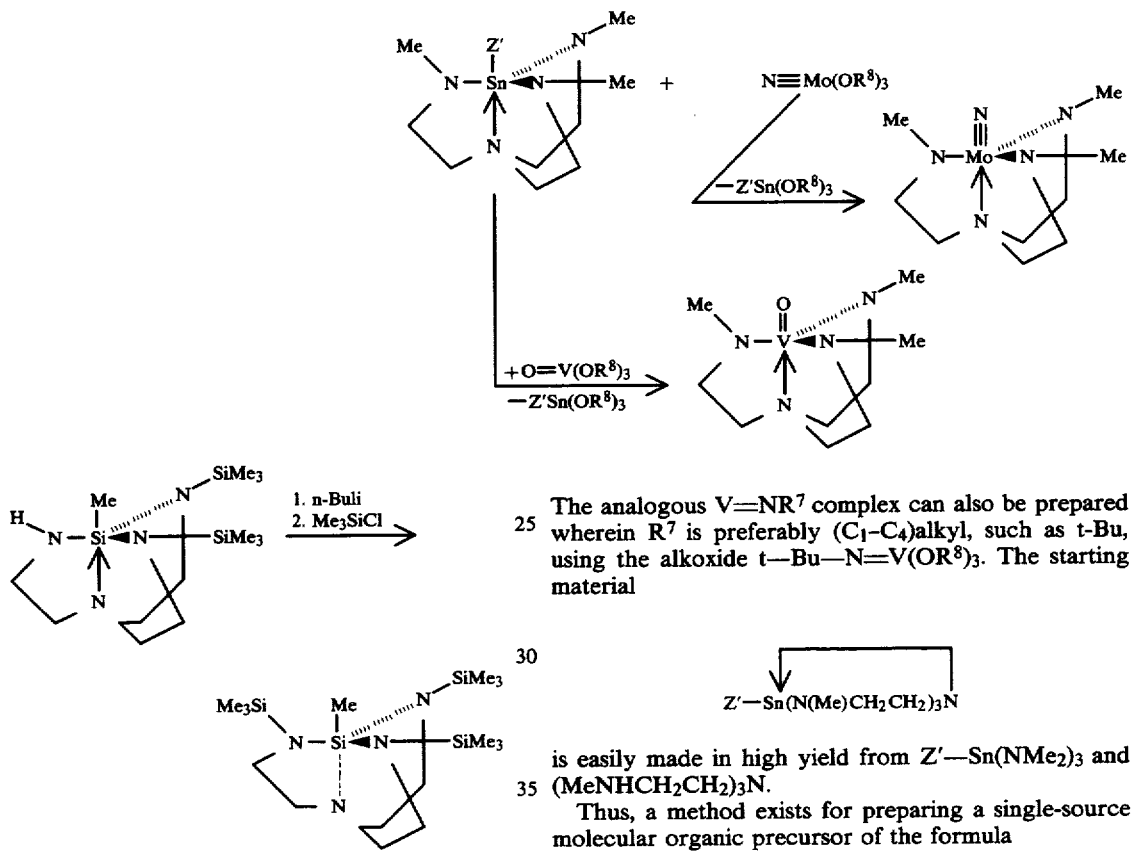

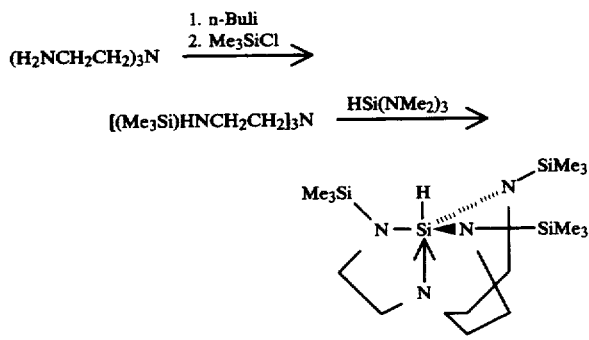

It should be noted in this example that the transannular bond in the final product of this reaction sequence, though severely stretched, is not broken completely by the strong steric interactions among the —CH$_3$ group ("Me") and the —N—SiMe$_3$ moieties around the silicon. Evidence for the persistence of an N→Si donor interaction exists. For example, the N—Si distance is appreciably shorter than the sum of the van der Waals radii, the donor nitrogen is in a planar environment, and the N—Si—N angles are larger than expected. An alternative two-step reaction sequence for the synthesis of such compounds is as follows:

$$(H_2NCH_2CH_2)_3N \xrightarrow[\text{2. Me}_3\text{SiCl}]{\text{1. n-BuLi}}$$

$$[(Me_3Si)HNCH_2CH_2]_3N \xrightarrow{HSi(NMe_2)_3}$$

In the product of this scheme, the transannular N→Si bond is intact since the hydrogen atom on the silicon is sterically nonbulky.

Furthermore, the novel transmetallation reactions below give nearly quantitative yields of the desired tricyclic products:

The analogous V=NR$^7$ complex can also be prepared wherein R$^7$ is preferably (C$_1$-C$_4$)alkyl, such as t-Bu, using the alkoxide t—Bu—N=V(OR$^8$)$_3$. The starting material $$Z'—Sn(N(Me)CH_2CH_2)_3N$$

is easily made in high yield from Z'—Sn(NMe$_2$)$_3$ and (MeNHCH$_2$CH$_2$)$_3$N.

Thus, a method exists for preparing a single-source molecular organic precursor of the formula $$Z—M(N(R^9)CH_2CH_2)_3N$$

comprising combining a metal alkoxide of the formula Z—M(OR$^8$)$_3$ and an azastannatrane of the formula $$Z'—Sn(N(R^9)CH_2CH_2)_3N.$$

In these starting materials Z', R$^8$, and R$^9$ are independently selected from the group consisting of hydrogen and (C$_1$-C$_4$)alkyl groups; M is a metal or metalloid selected from the group consisting of a lanthanide, an actinide, and a metal or a metalloid from Groups IIIA, IIIB, IV, IVB, VA, VB, VIB, VIIB, or VIIIB; and "Z" is selected from the group consisting of hydrogen, halides, and a ligand which bonds to M through N, O, P, S, As, Si, or C. The process involves use of equimolar amounts of the two starting materials, the use of a hydrocarbon or etheral solvent, preferably an ethereal solvent, such as tetrahydrofuran (THF), and a temperature of about 20°–120° C., preferably about 40°–100° C., and more preferably about 60°–80° C.

Another novel transmetallation reaction starting with an aluminum dimeric species gives nearly quantitative yields of the desired tricyclic V=NR$^7$ wherein R$^7$ is a (C$_1$-C$_4$)alkyl or a triorganosilyl group of the formula (R=($C_1$–$C_4$)alkyl), such as —$SiMe_3$. An example is as follows:

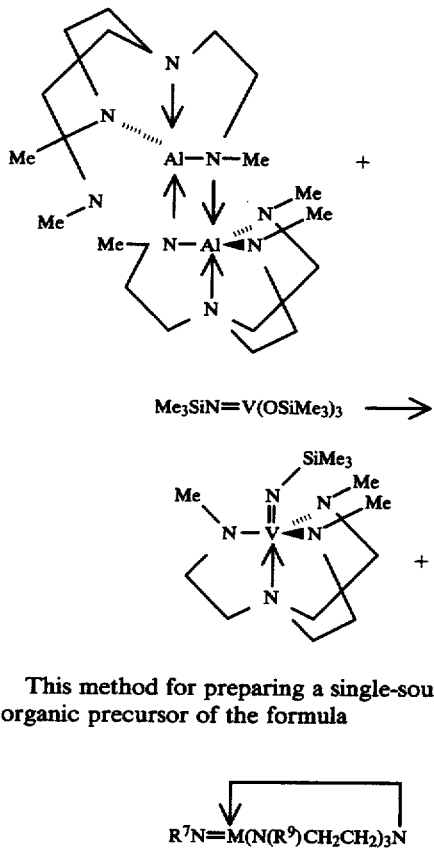

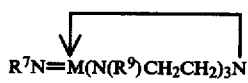

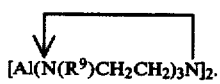

This method for preparing a single-source molecular organic precursor of the formula $$R^7N\!\!=\!\!M(N(R^9)CH_2CH_2)_3N$$

comprises combining a metal complex of the formula $R^7N\!\!=\!\!M(OSiR_3)_3$ and an aluminum azametalatrane of the formula $$[Al(N(R^9)CH_2CH_2)_3N]_2.$$

In these starting materials, R, $R^7$ and $R^9$ are as defined above; and M is a metal or metalloid selected from the group consisting of a lanthanide, an actinide, and a metal or a metalloid in Groups IIIA, IIIB, IVA, IVB, VA, VB, VIB, VIIB, or VIIIB. The process involves the use of a hydrocarbon or ethereal solvent, and a temperature of about 20°–120° C., preferably about 40°–100° C., and more preferably about 60°–80° C.

The ready accessibility of $P(CH_2CH_2PR^{10}H)_3$ ($R^{10}$=H, Me) makes it attractive to synthesize phosphide precursors of the compound type A using methods analogous to those discussed herein. Phosphorus-rich metal or metalloid phosphide films formed from such precursors display semiconduction properties. The films formed are of the formula $M_xP_y$ wherein x and y can be 1–4. Examples of these include MP (M=a lanthanide or a boron group element), $MP_2$ (M=Fe, Ru, Os), $MP_3$ (M=Rh), and $M_3P_4$ (M=Th). Synthetic routes analogous to those used to form phosphatranes of $P(CH_2CH_2PR^{10}H)_3$ can be used to make $As(CH_2CH_2AsR^{10}H)_3$, thus allowing the synthesis of the arsenide analogue of compounds of type A.

Chemical Vapor Deposition

Although any process of deposition may be used to deposit films using the single-source precursors of the present invention, chemical vapor deposition techniques are preferred. In a typical CVD process, a molecular organic precursor is volatilized and decomposed to yield a film on the target substrate. For a further discussion of CVD techniques see M. G. Hocking et al., *Metallic and Ceramic Coatings*, Longman Scientific and Technical: Essex, England, 1989, Chapter 4.

CVD techniques are typically classified into various types in accordance with the heating method, gas pressure, and/or chemical reaction. For example, conventional CVD methods include: (1) cold wall type CVD, in which only a deposition substrate is heated; (2) hot wall type CVD, in which an entire reaction chamber is heated; (3) atmospheric CVD, in which reaction occurs at a pressure of about one atmosphere; (4) low-pressure CVD in which reaction occurs at pressures from about $10^{-1}$ to 100 Torr; (5) electron-beam assisted CVD and ion-beam assisted CVD in which the energy from an electron-beam or an ion-beam directed towards the substrate provides the energy for decomposition of the precursor; (6) plasma-assisted CVD and photo-assisted CVD in which the energy from a plasma or a light source activates the precursor to allow depositions at reduced substrate temperatures; and (7) laser assisted CVD wherein laser light is used to heat the substrate or to effect photolytic reactions in the precursor gas.

In general, thermal CVD can be carried out in any type of apparatus in which the substrate and/or the gaseous precursor is heated. This can include standard thermal reactors such as cold wall/hot substrate reactors and hot wall type reactors. This can also include radiation beam reactors in which a beam, such as a laser beam, is used to heat the substrate and/or to decompose the precursor once volatilized. Heating of substrates in a cold wall CVD reactor may be accomplished by several methods including the use of hot stages or induction heating. A typical apparatus includes a gas-tight chamber or gas space having means for supporting a substrate, means for heating this substrate to a temperature above the decomposition temperature of the organometallic precursor, an inlet conduit for admitting carrier gas and/or vapor streams of the organometallic precursor, and an outlet conduit for removing a stream of decomposition products and undecomposed metal compound from the chamber, as well as carrier gas if used. Suitable apparatus of various types are well known in the art.

In a typical CVD process, the substrate on which deposition is to occur is placed in a reaction chamber, and is heated to a temperature sufficient to cause the decomposition of vapors of the precursor complex. When these vapors are introduced into the reaction chamber and transported to the vicinity of the substrate, they will decompose thereon to deposit a film containing the desired metal.

Any CVD apparatus design may be used in the present invention including hot wall reactors, cold wall reactors, radiation beam assisted reactors, plasma assisted reactors, and the like. In a thermal reactor CVD system, it is preferable that the decomposition reaction occur at the substrate. Thus, it is preferable to heat the substrate to a temperature in excess of the decomposition temperature of the precursor complex. In a radiation beam induced CVD technique, the radiation, such as from an ion beam, is preferably used to heat the substrate so that decomposition of the precursor occurs at the substrate.

These CVD processes can be used to provide blanket deposition of films on substrates, as well as to provide deposition on selected areas of the substrate, i.e., by use of a masking material, such as a resist material. Additionally, selected area depositions may be accomplished by energy beam assisted CVD where a beam of energy, such as an ion beam, selectively heats small portions of the substrate. For blank depositions, a cold wall-hot substrate reactor may sometimes be preferred because this design efficiently consumes the precursor. For selected area depositions, a radiation beam assisted reactor is preferred because the radiation beam can be used to "write" metal containing films onto small areas of the substrate.

Vacuum systems are typically used for CVD using the precursors of the present invention. There is no criticality with respect to the pressure in the system. Operating pressures of 1 to 100 mTorr can be used in the absence of carrier gas, and higher or lower pressures are also acceptable, i.e., up to about 2 Torr. These pressures are largely determined by the pumping speed of the vacuum equipment, the vapor pressure of the precursor complex, and carrier gases, which can optionally be added to increase the total pressure. When carrier gases are used, pressures may range from about 0.1 Torr to about 760 Torr (atmospheric pressure), and are more typically in the range of 20 to 300 Torr. However, this pressure does not appear to be highly critical to the deposition of the films.

Although it is preferred to conduct the present process without a carrier gas, it is often desirable to use a carrier gas in a CVD process, which is passed through or over the precursor. If used, a reactive carrier gas such as an oxygen-containing carrier gas (air, oxygen, or nitrous oxide), or ammonia, silane, hydrogen sulfide, and the like or combination of inert and reactive carrier gases may be used.

The method for applying a film to the surface of a substrate using the molecular organic precursors of the present invention preferably involves the thermal decomposition. In the method of the present invention, the surface of a substrate is exposed to a vapor to deposit a coating of $M_xE_y$ thereon. One specific type of CVD process useful in the method of the present invention is carried out in a flow-through reactor. This reactor is typically equipped with a sample chamber with a vessel containing the single-source precursor, a vacuum pump for vaporization of the precursor, a carrier stream of an inert gas if desired, a reaction chamber containing the substrate to be coated, and a means by which the sample and reaction chambers can be heated.

The precursor in a reactor of this type, or any chemical vapor deposition reactor, is generally maintained at a constant temperature during the vaporization process for ease of handling; however, this is not critical. This is not generally a requirement for effective deposition of films, however. This temperature is generally below the decomposition temperature of the precursor, but at a temperature such that the precursor is sufficiently capable of being volatilized in the process of chemical vapor deposition. Preferably, this temperature is about 25°–250° C., and more preferably about 50°–150° C.

The substrate is heated to a temperature required for decomposition of the precursor to the compound desired. Typically this occurs at a temperature of about 25°–250° C., and preferably at a temperature of about 50°–200° C. The substrate, heated to the precursor decomposition temperature, is exposed to the single-source precursor for a sufficient period of time such that a desired amount of the precursor is coated onto the surface of the substrate.

Typical chemical vapor deposition techniques allow for the deposition of films on substrates useful in the electronics, optics, or metals-on-polymers industries. Any substrate that is generally stable, i.e., does not substantially decompose, under the conditions employed in chemical vapor deposition techniques, are suitable for use. Useful substrates include, for example, silicon, tin oxide ($SnO_2$), gallium arsenide (GaAs), aluminum oxide, silica, glass, quartz, polyimide, polymethyl-methacrylate, and other polymers. Additional substrates that can be coated with films using the precursors of the present invention include synthetic fibers and fabrics, graphite, metals, nonmetallic refractories, ceramic materials, and cermets. It is to be understood, however, that the method of the present invention is not limited to the above-listed materials because it is not typically substrate specific. Furthermore, the single-source precursors are not generally limited to use on any specific substrate. Prior to initiating CVD, the substrates are typically pre-cleaned by the standard means of sequential soaking in baths of tetrachloroethane, methanol, distilled water, dilute hydrofluoric acid, and distilled water.

Precursors of the present invention are also useful in molecular beam epitaxy ("MBE") and chemical beam epitaxy ("CBE") processes. In MBE or CBE, the precursors are introduced into a vacuum chamber and expanded to form molecular beams. The molecular beams strike the hot substrate and deposit films. In MBE and CBE processes the reactor pressure is typically about $10^{-5}$ Torr during crystal growth, i.e., while the MOCVD precursors are actually being supplied to the substrate, with a typical background pressure of about $10^{-10}$ to $10^{-}$ Torr. The low background pressure in MBE allows for fast switching of material composition, which is important in growing ultra thin layers and other multi-layer coatings in which there are abrupt composition and sloping changes from layer to layer. Thus, in these processes, multi-layer structures of well defined composition and sharp interfacial boundaries are typically produced. Thus, multiple layer coatings having different compositions are best achieved with MBE or CBE.

Herein, the films produced can be represented by the formula "$M_xE_y$" wherein there can be one type of "M" atom and one type of "E" atom, or there can be two or more types of "M" atoms and two or more types of "E" atoms in a particular film. For example, the films can include Al and Ga. Such alloy compositions can be formed by volatilizing heterobimetallic dimeric compounds as discussed above, or by simultaneously volatilizing two different compounds. Furthermore, the single-source molecular organic precursors of the present invention can include more than one type of "E" element, resulting in mixed species in the films, such as oxide-nitride films. The values of "x" and "y" in "$M_xE_y$" can be any number as required by the particular combination of elements, such that stable films are formed. Typically, however, x=1–5, which represents the total number of "M" atoms whether the same or different, and y=1–5, which represents the total number of "E" atoms whether the same or different.

The MOCVD agents, i.e., precursors, volatilized and decomposed to form the $M_xE_y$ films of the present invention are represented by the generalized formula

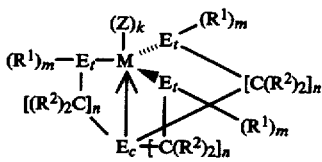

as described above. It is preferred that the elements directly bonded to the central metal or metalloid "M" be the same. That is, it is preferred that all the "$E_c$" and "$E_t$" atoms in the tetradentate tripodal ligand be the same element, i.e., either all N, all P, or all As, and that the "Z" ligand be bonded to "M" through an atom of this same element. In this way, the preferred films of the present invention are nitrides, phosphides, and arsenides. It is to be understood, however, that mixed films are within the scope of the present invention. For example, mixed oxide-nitride films, "$E_t$" is preferably an N and at least one of the "$E_t$" atoms is an O, more preferably at least one of the "$E_t$" atoms is an O and at least one of the "$E_t$" atoms is an N.

Most preferably the films formed by the method of the present invention are nitride films. For the deposition of relatively pure nitride films, i.e., those with little or no impurities, such as carbide impurities, all the atoms directly bonded to the metal or metalloid "M" in the precursor is an N atom. These compounds are known as azametalatranes or "pnictides" and the film deposited is a nitride of the formula $M_xN_y$ (wherein x and y are typically 1-5), such as TiN, $Zr_3N_4$, VN, $Mo_3N_4$, FeN, BN, AlN, GaN, InN, SiN, and the like. These metallic and metalloid. nitrides typically possess useful properties for the microelectronics industry, such as high temperature semiconduction, insulating thermal conduction, piezoelectric characteristics, thermal shock stability, light emission capabilities, device capping/-protection, and extreme wear resistance.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL SECTION

General Procedures

All reactions were carried out under an atmosphere of prepurified argon at room temperature by using standard inert-atmosphere and Schlenk techniques unless otherwise stated. Tetrahydrofuran (THF), toluene, benzene, pentane, and $Et_2O$ were distilled from Na/benzophenone under $N_2$. Triethanolamine (TEA) was distilled under vacuum and stored over type 4A molecular sieves. Hexane and chloroform were distilled from phosphorus(V) oxide ($P_2O_5$) under argon. Dichloromethane was distilled from calcium hydride under argon. $^1H$ NMR and $^{13}C$ NMR spectra were recorded on a Nicolet TM NT-300 300-MHz spectrometer using the proton impurity of the solvent as the internal reference. $^{11}B$ NMR, $^{27}Al$ NMR, $^7Li$ NMR, and $^{29}Si$ NMR were performed on Varian TM VXR-300 300-MHz spectrometer. Variable-temperature NMR spectra were obtained on a Bruker TM WM-200 200-MHz or a Varian TM VXR-300 300-MHz instrument. Fourier transform infrared (FT-IR) spectra were recorded on an IBM-IR98 spectrometer as solids in KBr pellets or Nujol mulls. Mass spectra were obtained on a Finnigan TM 4000 instrument or a Kratos TM MS-50 spectrometer. Melting points were determined by a Thomas Hoover capillary apparatus, and are uncorrected.

The ligands referred to as TEA (($HOCH_2CH_2)_3N$, triethanolamine) and Tren (($H_2NCH_2CH_2)_3N$, tris(2-aminoethyl)amine) are available from Aldrich TM Chemical Company, Milwaukee, Wis. The ligand referred to as Me-Tren (($MeHNCH_2CH_2)_3N$) was prepared according to the method of H. Schmidt et al., Z. Anorg. Allg. Chem., 578, 75 (1989), which is incorporated herein by reference. The preparation involves the reaction of Tren with ethylchloroformate, isolation of the intermediate, which is then combined with $LiAlH_4$. The ligand referred to as TMS-Tren (($Me_3SiNCH_2CH_2)_3N$, tris[2-(trimethylsilylamino)ethyl]amine) was prepared according to the method of D. Gudat et al., Organometallics, 8, 2772 (1989), which is incorporated herein by reference. The preparation involves the initial reaction of Tren with n-butyllithium in hexanes followed by the addition of trimethylchlorosilane. The ligand $N(CH_2CH_2OH)_2(CH_2CH_2NH_2)$ was prepared according to the method of R. D. Peck et al., J. Am. Chem. Soc., 81, 3984 (1959), which is incorporated herein by reference. The preparation involves the reaction of monoacetylethylenediamine with ethylene oxide followed by the addition of HCl to form a chloride salt, which is then converted to the free base with KOH.

The following "metalatranes"

and "azametalatranes"

were obtained in high yields as either crystalline solids or amorphous solids. Under a vacuum of about $1 \times 10^{-2}$ Torr, many of these complexes decompose upon attempted sublimation. Under a higher vacuum, such as $1 \times 10^{-3}$ Torr, however, most sublime. For example, in the high vacuum of a mass spectrometer, the titanatranes and azatitanatranes display parent ions for the monomeric cage units.

Titanium Type B Compounds

Preparation of (2-Methyl-2-propanolato)titanatrane (t-BuO-Ti(OCH$_2$CH$_2$)$_3$N). A solution of 3.46 g (10.2 mmol) Ti(O-t-Bu)$_4$ (prepared by the method of R. J. Speer, J. Org. Chem., 14, 655 (1949), which is incorporated herein by reference) in 15 mL of THF was added dropwise to a solution of 1.49 g (10.0 mmol) of TEA in 20 mL of THF and stirred for 30 min. The volatiles were removed under vacuum, and the crude product was recrystallized from benzene: 2.40 g, 90% yield of colorless crystals; mp 156°-158° C. $^1H$ NMR (CDCl$_3$): δ1.38 (s, 9 H), 3.15 (t, 6 H), 4.42 (t, 6 H). $^{13}C$ NMR (CDCl$_3$): δ31.47 (CH$_3$), 55.81 (CH$_2$N), 70.16 (CO). MS (EI): m/e 252 (M+ −CH₃, 100%), 237 (M+ −C₂H₆, 64%), 207 (M+ −C₃H₈O, 23%), 194 (M+ −C₄H₉O, 65%). IR (KBr, cm⁻¹): 1261 w, 1230 w, 1193 w, 1103 s, 1064 vs, 1010 s, 923 w, 900 m, 792 w, 590 m (ν(Ti-OR)). HRMS (EI) for M+ −CH₃, C₉H₁₈NO₄Ti: found, m/e 252.07082; calcd, m/e 252.07153.

An alternative preparation method involves combining a stoichiometric amount of t-BuOH with (dimethylamino)titanatrane, synthesized as discussed below, in methylene chloride. After being stirred for 10–30 min, the reaction mixture was layered with pentane and cooled to −25° C. Colorless crystals were separated and characterized by ¹H NMR and ¹³C NMR spectroscopy. The yield was better than 90%. Variable temperature solution NMR indicated that (2-methyl-2-propanolato)titanatrane exhibits monomeric behavior at room temperature.

Preparation of (Phenolato)titanatrane

(PhO—Ti(OCH₂CH₂)₃N).

A solution of 3.40 g (10.0 mmol) Ti(O-t-Bu)₄ in 10 mL of THF was added dropwise to 0.94 g (10.0 mmol) of phenol in 15 mL of THF and stirred for 1 h. TEA (1.49 g, 10.0 mmol) in 10 mL of THF was added dropwise to the yellow solution. Stirring was continued for an additional 1 h. The volatiles were removed under vacuum, and the yellow crude product was dried under vacuum for 17 h at 60° C.; 2.45 g, 85% yield; mp 95°–105° C. ¹H NMR (CDCl₃): δ3.30 (br s, ν½=30 Hz, 6 H), 4.58 (br s, ν½=30 Hz, 6 H), 6.7–7.2 (m, 5 H). ¹³C NMR (CDCl₃, 60° C.): δ58.65 (CH₂N), 72.14 (CH$_b$₂O), 118.43, 119.63, 126.6. HRMS (EI) for M+ −C₁₂H₁₇NO₄Ti: found, m/e 287.06400; calcd, m/e 287.6370. IR (Nujol, cm⁻¹): 1587 s, 1481 s, 1269 s, 1097 s, 1072 vs, 881 m, 757 m, 648 m, 558 m, 512 m.

An alternative preparation method involves combining a stoichiometric amount of PhOH with (dimethylamino)titanatrane, synthesized as discussed below, in methylene chloride. After being stirred for 10–30 min, the reaction mixture was layered with pentane and cooled to −25° C. Colorless crystals were separated and characterized by ¹H NMR and ¹³C NMR spectroscopy. The yield was better than 90%. Variable temperature solution NMR indicated that (phenolato)titanatrane exhibits fluxional dimeric behavior at room temperature, becoming monomeric upon warming.

Preparation of (Acetato)titanatrane

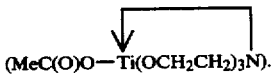

(MeC(O)O—Ti(OCH₂CH₂)₃N).

This synthesis was analogous to that of (phenolato)titanatrane using acetic acid in place of phenol. The crude product was recrystallized from chloroform; 2.08 g, 82% yield; mp 185°–186° C. ¹H NMR (CDCl₃): δ 2.03 (s, 3 H), 3.30 (br s, ν½=165 Hz, 6 H), 4.65 (br s, ν½=45 Hz, 6 H). ¹H NMR (CDCl₃, 60° C.): δ2.05 (s, 3 H), 3.47 (t, 6 H), 4.73 (t, 6 H). ¹H NMR (CD₂Cl₂, −60° C.): δ 2.01 (s, 3 H), 3.14–3.22 (m, 4 H), 3.94 (virt dt, 2 H), 4.41 (virt dd, 2 H), 4.60–4.76 (virt t+dt, 4 H). ¹³C NMR (CDCl₃, 60° C.): δ 23.29 (CH₃), 62.32 (CH₂N), 74.20 (CH₂O), 186.31 (C=O). MS (EI): m/e 253 (M+, 0.2%), 238 (M+ −CH₃, 10.7%), 223 (M+ −CH₂O, 100%), 193 (M+ −CH₃CO₂H, 58.9%). IR (KBr, cm⁻¹): 1577 s, 1446 s, 1085 s, 1070 vs, 1035 s, 1028 s, 921 m, 902 s, 688 m, 651 m, 622 m, 597 m.

A crystal structure was done of a colorless crystal of (acetato)titanatrane. The complex is a dimer in the solid state with alkoxide bridging. A striking feature of the structure is the seven-coordinate nature of the titanium atoms as a result of this bridging and bidentate acetate groups. This contrasts with the six-coordinate octahedral geometry typically found in other titanium alkoxides. The geometry around each titanium atom can be viewed as a distorted trigonal prism of oxygen atoms with a nitrogen near a rectangular face. The separation (131 cm⁻¹) in the carboxyl stretches (1577, 1446 cm⁻¹) in the KBr IR spectrum of this compound is in agreement with bidentate acetato coordination. Variable temperature solution NMR indicated that (acetato)titanatrane exhibits fluxional dimeric behavior at room temperature, becoming monomeric upon warming.

Preparation of (Dimethylamino)titanatrane

(Me₂N—Ti(OCH₂CH₂)₃N).

A solution of 0.64 g (4.3 mmol) of TEA in 20 mL of THF is added in one portion to a stirred solution of 1.00 g (4.5 mmol) of Ti(NMe₂)₄ (prepared by the method of D. C. Bradley, J. Chem. Soc., 3857 (1960), which is incorporated herein by reference) dissolved in 20 mL of THF and stirred overnight. A yellow microcrystalline solid separated from the solution. The volatiles were removed under vacuum, and the crude product was recrystallized from THF in 84% yield; decomposed upon heating. ¹H NMR (C₆D₆): δ 2.23–2.37 (m, 4 H), 2.69 (virt q, 2 H), 3.74 (s, 6 H), 4.24 (t, 2 H), 4.33–4.52 (m, 4 H). ¹³C NMR (C₆D₆): δ50.97 (CH₃N), 57.49 (CH₂N), 62.95 (2×CH₂N), 69.37 (CH₂O), 71.48 (2×CH₂O). ¹³C NMR (C₆D₆, 60° C.): δ50.27 (CH₃N), 61.69 (CH₂N), 70.96 (CH₂O). Anal. Calcd for C₈H₁₈N₂O₃Ti: C, 40.38; H, 7.61; N, 11.38. Found: C, 40.35; H, 7.62; N, 11.76.

A crystal structure was done of a yellow crystal of (dimethylamino)titanatrane. The complex is a dimer in the solid state with alkoxide bridging. Variable temperature solution NMR indicated that (dimethylamino)titanatrane exhibits rigid dimeric behavior at room temperature. It is labile to substitution of the axial NMe₂ group by a variety of —OR groups, such as O—i—Pr, OSiPh₃, O—t—Bu, OPh, and OCMe₂Et, in reactions with the corresponding ROH reagent.

Preparation of

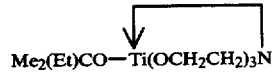

Me₂(Et)CO—Ti(OCH₂CH₂)₃N (Dimethylamino)titanatrane (0.52 g, 2.2 mmol), prepared as described above, was reacted with tert-amyl alcohol (0.23 mL, 0.19 g, 2.2 mmol) in 20 mL of dry methylene chloride. After being stirred for 10 min at room temperature, the color changed from yellow to colorless, indicating the end of the reaction. The contents of the reaction flask were layered with pentane and cooled at −25° C. Small crystals grew overnight in 96% yield. $^1$H NMR (CDCl$_3$): δ0.94 (t, 3 H, $^3J_{HH}$=7.5 Hz, CH$_3$CH$_2$), 1.29 (s, 6 H, (CH$_3$)$_2$), 1.59 (q, 2 H, $^3J_{HH}$=7.5 Hz, CH$_3$CH$_2$), 3.11 (t, 6 H, $^3J_{HH}$=5.4 Hz, NCH$_2$), 4.39 (t, 6 H, $^3J_{HH}$=5.4 Hz, OCH$_2$). $^{13}$C NMR (CDCl$_3$): δ9.10 (CH$_2$CH$_3$), 28.94 ((CH$_2$)$_2$), 36.99 (CH$_2$CH$_3$), 55.79 (CH$_2$N), 70.15 (CH$_2$O), 84.61 (CMe$_2$Et). IR (Nujol, cm$^{-1}$): 2979, 2845, 2682, 1463, 1376, 1357, 1026, 815, 452. MS m/e (relative intensity): 266 (25, M$^+$−Me), 252 (100, M$^+$−Et), 251 (54, M$^+$−2Me), 210 (1, M$^+$−CMe$_2$Et). Anal. Calcd for C$_{11}$H$_{23}$NO$_4$Ti: C, 46.99; H, 8.24; N, 4.98. Found: C, 46.83; H, 7.96, N, 5.07. Variable temperature solution NMR indicated that this alkoxy titanatrane exhibits monomeric behavior at room temperature.

Preparation of

[EtS—Ti(OCH$_2$CH$_2$)$_3$N]$_2$

To a solution of (dimethylamino)titanatrane (0.48 g, 2.0 mmol) in 20 mL of dry methylene chloride was added 0.15 mL (2.0 mmol) of ethanethiol. The reaction mixture was stirred for 4 h at room temperature and then layered with pentane and cooled at 0° C. Yellow microcrystals appeared overnight in 87% yield; mp 92° C., decomposed. $^1$H NMR (CDCl$_3$): δ1.26 (t, 6 H, $^3J_{HH}$=7.5 HZ, CH$_2$CH$_3$), 2.89 (t, 4 H, $^3J_{HH}$=5.1 Hz, CH$_2$N), 3.08–3.18 (m, 4 H, CH$_2$N), 3.38 (q, 4 H, $^3J_{HH}$=7.5 Hz, CH$_2$CH$_3$), 3.42-352 (m, 4 H, CH$_2$N), 4.53 (t, 4 H, $^3J_{HH}$=5.1 Hz, CH$_2$O), 4.65–4.74 (m, 4 H, CH$_2$O), 4.87–4.96 (m, 4 H, H$_2$O). $^{13}$C NMR (CDCl$_3$): δ19.72 (CH$_2$CH$_3$), 29.95 (CH$_2$CH$_3$), 57.21 (NCH$_2$), 60.73 (2 C, NCH$_2$), 72.83 (2 C, OCH$_2$), 75.84 (OCH$_2$). IR (Nujol, cm$^{-1}$): 2955, 2924, 2853, 1462, 1377, 1341, 1057, 901, 722, 567. MS m/e (relative intensity): 255 (5, M$^+$), 226 (1, M$^+$−Et), 194 (17, M$^+$−SEt). Variable temperature solution NMR indicated that this thiolatotitanatrane exhibits dimeric behavior between the temperatures of −55° C. and +55° C.

Preparation of

[i-PrS—Ti(OCH$_2$CH$_2$)$_3$N]$_2$

The procedure is similar to that for the preparation of

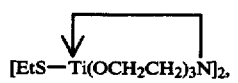
[EtS—Ti(OCH$_2$CH$_2$)$_3$N]$_2$, using isopropylthiol in place of ethanethiol; yield 92%; mp 112°–115° C., decomposed. $^1$HNMR (CDCl$_3$): δ1.29 (d, 12 H, $^3J_{HH}$=6.6 HZ, CH(CH$_3$)$_2$), 2.90 (t, 4 H, $^3J_{HH}$=5.1 HZ, NCH$_2$), 3.09–3.16 (m, 4 H, NCH$_2$) 3.43–3.52 (m, 4 H, NCH$_2$), 4.08 (h, 2 H, $^3J_{HH}$=6.6 Hz, CH(CH$_3$)$_2$), 4.56 (t, 4 H, $^3J_{HH}$=5.1 Hz, OCH$_2$), 4.72–4.80 (m, 4 H, OCH$_2$), 4.84–4.91 (m, 4 H, OCH$_2$). $^{13}$C NMR (CDCl$_3$): δ28.25 (CH(CH$_3$)$_2$), 40.09 (CH(CH$_3$)$_2$), 57.40 (NCH$_2$), 61.85 (2 C, NCH$_2$), 73.50 (2 C, OCH$_2$), 76.29 (OCH$_2$). IR (Nujol, cm$^{-1}$): 2951, 2923, 2852, 1457, 1375, 1097, 903, 639, 540. MS m/e (relative intensity): 269 (35, M$^+$), 254 (2, M$^+$−Me), 239 (13, M$^+$−2Me), 226 (1, M$^+$−CHMe$_2$), 194 (100, M$^+$−SCHMe). Variable temperature solution NMR indicated that this thiolatotitanatrane exhibits dimeric behavior between the temperatures of −55° C. and +55° C.

Preparation of

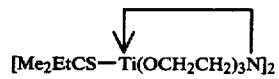
[Me$_2$EtCS—Ti(OCH$_2$CH$_2$)$_3$N]$_2$ (Dimethylamino)titanatrane (0.28 g, 1.2 mmol) was reacted with 0.12 g (0.15 mL, 1.2 mmol) of 2-methyl-2-butanethiol in THF (30 mL). The suspension was stirred at room temperature for 3 h under an inert atmosphere. The solvent was then removed under vacuum, and the product was dissolved in hot toluene and stored at −25° C. After 12 h, the pure yellow microcrystalline product was separated in 88% yield; decomposed on heating. $^1$H NMR (CDCl$_3$): δ0.86 (t, 6 H, $^3J_{HH}$=7.2 Hz, CH$_2$CH$_3$), 1.43 (s 12 H, C(CH$_3$)$_2$), 1.65 (q, 4 H $^3J_{HH}$=7.2 Hz, CH$_2$CH$_3$), 2.93 (t, 4 H, $^3J_{HH}$=7.4 Hz, NCH$_2$), 3.07–3.12 (m, 4 H, NCH$_2$), 3.41–3.51 (m, 4 H, NCH$_2$), 4.58 (t, 4 H, $^3J_{HH}$=7.4 Hz, OCH$_2$), 4.68–4.74 (m, 4 H, OCH$_2$), 4.82–4.91 (m, 4 H, OCH$_2$). $^{13}$C NMR (CDCl$_3$): δ10.04 (CH$_2$CH$_3$), 31.73 (C(CH$_3$)$_2$), 39.12 (CH$_2$CH$_3$), 51.99 (C(CH$_3$)$_2$), 57.76 (CH$_2$N), 64.17 (2 C, CH$_2$N) 73.96 (2 C, CH$_2$O), 75.50 (CH$_2$O). IR (Nujol, cm$^{-1}$): 2955, 2922, 2851, 1459, 1376, 1260, 1069, 1026, 800, 647, 564. MS m/e (relative intensity): 297 (10, M$^+$), 282 (1, M$^+$−Me) 268 (20, M$^+$−Et), 267 (3, M$^+$−2Me), 276 (1, M$^+$−CMe$_2$Et), 194 (100, M$^+$−SCMe$_2$Et) . Anal. Calcd for C$_{11}$H$_{23}$NO$_3$STi: C, 44.45; H, 7.80. Found: C, 44.94; H, 7.87 . Variable temperature solution NMR indicated that this thiolatotitanatrane exhibits dimeric behavior between the temperatures of −55° C. and +55° C.

Preparation of

[PhS—Ti(OCH$_2$CH$_2$)$_3$N]$_2$

In a 100-mL round-bottomed flask equipped with a side arm, (dimethylamino)titanatrane (0.38 g, 1.6 mmol) was suspended in 50 mL of THF and 0.16 mL (0.17 g, 1.5 mmol) of benzenethiol was added dropwise. Upon addition of the benzenethiol, the color changed from yellow to bright orange. The reaction was refluxed for 1 h. The solvent was removed and the orange solid crystallized from hot toluene in 85% yield; mp 113°–115° C. with some decomposition. $^1$H NMR (CDCl$_3$): δ2.93 (t, 4 H, $^3J_{HH}$=5.4 Hz, NCH$_2$), 3.14–3.22 (m, 4 H, NCH$_2$), 3.44–3.51 (m, 4 H, NCH$_2$) 4.58–4.85 (m, 12 H, OCH$_2$), 6.78–7.12 (m, 10 H, C$_6$H$_5$). $^{13}$C NMR (CDCl$_3$): δ57.26 (NCH$_2$), 60.29 (2 C, NCH$_2$), 72.99 (2 C, OCH$_2$), 75.98 (OCH$_2$), 124.07 (p-C$_6$Hs), 127.79 (o-C$_6$H$_5$), 130.67 (m-C$_6$H$_5$). IR (Nujol, cm$^{-1}$): 3100, 3050, 2951, 2922, 2851, 1576, 1461, 1377, 1251, 1091, 1028, 900, 802, 748, 646, 616, 547. MS m/e (relative intensity): 303 (9, M$^+$), 194 (36, M$^+$−SPh). Anal. Calcd for C$_{12}$H$_{17}$NO$_3$STi: C, 47.54; H, 5.65. Found: C, 46.86, H, 4.96. Variable temperature solution NMR indicated that this thiolatotitanatrane exhibits dimeric behavior between the temperatures of −55° C. and +55° C.

Preparation of

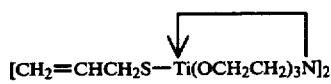

The procedure was similar to the preparation of

using allylthiol in place of ethanethiol. Pure compound was obtained after several recrystallizations from $CH_2Cl_2$/pentane in 45% yield; mp=131°-132° C. (with some decomposition). $^1H$ NMR ($CDCl_3$): δ2.92 (t 4 H, $^3J_{HH}$=5.4 Hz, $NCH_2$), 3.14–3.21 (m, 4 H, $NCH_2$), 3.46–3.55 (m, 4 H, $NCH_2$, 4.05) (dd, 4 H, $^3J_{HH}$=7.2 Hz, $^4J_{HH}$=0.9 Hz, $SCH_2$), 4.50 (t, 4 H, $^3J_{HH}$=7.2 Hz, $OCH_2$), 4.56–4.75 (m, 4 H, $OCH_2$), 4.81–4.88 (m, 2 H, $OCH_2$), 4.91–4.99 (m, 4 H, $CH_2CH$), 5.05–5.12 (m, 2 H, $CH_2CH$), 5.90–6.04 (m, 2 H, $CHCH_2$). $^{13}C$ NMR (75.4 MHz, $CDCl_3$): δ38.5 ($SCH_2CH=CH_2$), 57.20 ($NCH_2$), 60.57 (2 C, $NCH_2$), 72.83 (2 C, $OCH_2$), 75.97 ($OCH_2$), 113.34 ($SCH_2CH=CH_2$), 139.91 ($SCH_2CH=CH_2$). IR (Nujol, $cm^{-1}$): 2958, 2846, 1457, 1259, 1100, 1075, 1030, 802, 729, 603. MS m/e (relative intensity): 267 (1, $M^+$), 226 (1, $M^+$−allyl), 194 (31, $M^+$−S(allyl)). Variable temperature solution NMR indicated that this thiolatotitanatrane exhibits dimeric behavior between the temperatures of −55° C. and +55° C.

Preparation of

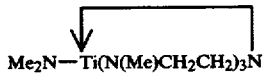

In 15 mL of THF was dissolved 1.09 g (4.89 mmol) of $Ti(NMe_2)_4$ and 0.92 g (4.89 mmol) of Me-Tren. The mixture was heated to 60° C. and stirred for 2 h. The initially yellow solution turned red, and dimethylamine was evolved. The solvent was removed under vacuum and the crude product vacuum distilled (116°-120° C. at 114 Torr). A red oil was obtained, which solidified upon standing for several days; yield 55%. $^1H$ NMR ($C_6D_6$): δ2.59 (t, 6 H, $NCH_2$), 3.16 (t, 6 H, $NCH_2$), 3.27 (s 15 H, $NCH_3$, $N(CH_3)_2$). $^{13}C$ NMR ($C_6D_6$): δ43.63 ($CH_3N$), 45.43 ($CH_3N$), 52.51 ($CH_2N$), 58.75 ($CH_2N$). HRMS (EI): m/e 277.17630 (calcd for $C_{11}H_{27}N_5Ti$ 277.17459; error +1.53 ppm). Variable temperature solution NMR indicated that this azatitanatrane exhibits monomeric behavior at room temperature.

Preparation of

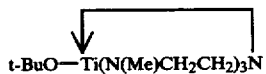

A solution of 0.31 g (4.2 mmol) of tert-butyl alcohol in 10 mL of toluene was added dropwise to a solution of 1.00 g (4.5 mmol) of $Ti(NMe_2)_4$ in 10 mL of toluene. After the mixture was stirred at room temperature for 30 min, a solution of 0.80 g (4.3 mmol) of Me-Tren was added. The reaction mixture was kept at 60° C. for an additional 2 h. The volatiles were removed under vacuum and the crude product was purified by sublimation (twice) at 90°-100° C. (38 Torr). The pure product was obtained in 54% yield. $^1H$ NMR ($C_6D_6$): δ1.57 (s, 9 H, $(CCH_3)_3$), 2.69 (t, 6 H, $NCH_2$), 3.15 (t, 6 H, $NCH_2$), 3.43 (s, 9 H, $NCH_3$). $^{13}C$ NMR ($C_6D_6$): δ32.89 (($CH_3)_3C$), 48.45 ($CH_3N$), 52.87 ($CH_2N$), 58.47 ($CH_2N$), 80.21 (CO). HRMS (EI): m/e 308.19045 (calcd for $C_{13}H_{30}N_4OTi$ 306.18941; error+1.78 ppm). Anal. Calcd for $C_{13}H_{30}N_4OTi$: C, 50.9; H, 9.80; N, 18.30. Found: C, 50.53; H, 9.83; N, 18.12. Variable temperature solution NMR indicated that this azatitanatrane exhibits monomeric behavior at room temperature.

Silicon Type B Compounds

Preparation of 1-Azidoazasilatrane

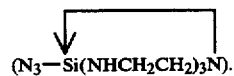

To a filtered solution of 0.71 g (4.1 mmol) of azasilatrane

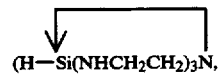

prepared by the method of D. Gudat et al., Organometallics, 8, 2772 (1989), which is incorporated herein by reference) in 20 mL of dry $CH_3CN$ was added 0.55 mL (4.2 mmol ) of $Me_3SiN_3$ (available from Aldrich ™ Chemical Co., purified by distillation). Over a period of about 2 h, crystals of

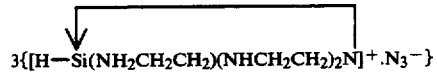

formed (mp 138°-140° C., with some decomposition). FT-IR (KBr, $cm^{-1}$): 3376 s, 3321 s, 2037 vs (N≡N stretch), 2023 vs (Si-H stretch), 1601 m (NH). $^1H$ NMR ($CDCl_3$): 2.61 t, 2.86 t ($CH_2$ cage protons of

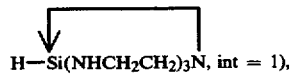

2.65 t, 2.99 t ($CH_2$cage protons of

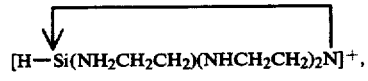

int=1), 4.27 s (br, NH, $NH_2$), 4.67 s

(SiH of H—Si(NH₂CH₂CH₂)(NHCH₂CH₂)₂N]⁺).

Elemental Anal. Calc. (found) for C₂₄H₆₇N₂₅Si₄: C, 35.22 (35.44): H, 8.25 (8.56): N. 42.79 (42.79); Si, 13.73 (13.45).

These freshly prepared crystals (0.72 g, 0.88 mmol) when heated became molten at approximately 180° C. under N₂. Heating was continued (approximately 15 min) until gas evolution ceased. The solid residue was sublimed under vacuum at 60°-140° C. and 10⁻³ Torr, affording 0.15 g (7.0 mmol, 80%) of crude 1-azidoazasilatrane, contaminated with approximately 5% of Tren as shown by ¹H NMR spectroscopy. A second vacuum sublimation at 110°-135° C. and 10⁻³ Torr afforded 80 mg of pure 1-azidoazasilatrane, mp>275° C. Anal. Calcd (found): C, 33.78 (33.40); H, 7.09 (7.01); N, 45.96 (44.57); Si, 13.17 (13.41). MS (EI, 70 eV): m/e 213.1160 (calcd for M⁺, 213.11583), 183.0818 (calcd for (M⁺−H₂C=NH₂), 183.0816), 171.1066 (calcd for (M⁺−N₃), 171.1066). ¹H NMR (CDCl₃): δ3.10 t (6 H, ³J$_{HH}$=5.92 Hz, H₂CN$_{ax}$), 2.81 t (6 H, H₂CN$_{eq}$), 1.24 (3 H, NH). IR (KBr, cm⁻¹): 3447 s, 3431 s, 2104 vs (N≡N stretch), 1600 br (NH, NH₂ bend).

Preparation of 1-(Thiocyanato)azasilatrane

(NCS—Si(NHCH₂CH₂)₃N)

Trimethylsilylthiocyanato (Me₃SiNCS) (0.7 mL, 4.54 mmol, available from Aldrich ™ Chemical Co., purified by distillation) was added to a solution of 0.71 g (4.12 mmol) of azasilatrane in 15 mL of CH₃CN at room temperature. The resulting precipitate was dissolved in the mother liquor by heating the latter to its boiling point (82° C.). The hot solution was filtered and cooled slowly to 0° C., affording pure

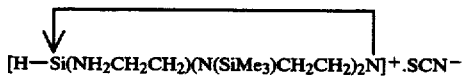
[H—Si(NH₂CH₂CH₂)(N(SiMe₃)CH₂CH₂)₂N]⁺.SCN⁻

(as indicated by ²⁹Si MAS NMR spectroscopy) as large colorless crystals suitable for X-ray diffraction studies. The crystals were filtered, rinsed with benzene (2×3 mL), and dried under vacuum (yield 0.44 g, 29%). The filtrate was refrigerated overnight at approximately −20° C., affording a second crop (0.15 g, 10%) of crystals, mp 116° C., decomposed. ¹H NMR (CDCl₃): δ 4.42 s (1 H, SiH), 2.98 t (broad, 4 H, ³J$_{HH}$=5.9 Hz, H₂C(6), H₂C(11)), 2.93 t (H₂C(3)), 2.89 t (broad, 4 H, H₂C(4), H₂C(7)), 2.82 t (broad, 2 H, ³J$_{HH}$=5.7 H₂C(3)), 0.12 s (18 H, Si(CH₃)₃). MS (CI—NH₃): m/e 317 (M⁺(of cation), 30%), 315 (M⁺−2, 6%), 245 (M⁺−72 (Me₃SiCH₂), 16%), 173 (M⁺−144, 100%). MS (EI, 70 eV): m/e 315 (M⁺(of cation) −2, 25%), 243 (M⁺−72, 13%), 171 (M⁺−144, 100%). IR (KBr, cm⁻¹): 3368 s, 3327 s, 2062 s (N≡C stretch), 1612 s (NH, NH₂ bend).

These freshly prepared crystals (0.57 g, 1.5 mmol) were heated at 140° C. for 15 min. The resulting residue was freed from volatile liquids by vacuum distillation of the liquids into a cold trap and then sublimed under vacuum (10⁻⁸ Torr) at 110°-150° C. to give pure 1-(thiocyanato)azasilatrane; yield 33%; mp>200° C. MS (EI, 70 eV): m/e 229.0818 (calcd for M⁺ 229.08175), 199.0473 (calcd for M⁺−H₂C=NH₂, 199.04736), 187.0467 (calcd for M⁺−CH₃CNH, 187.0474), 171.1053 (calcd for M⁺−SCN, 171.1066). ¹H NMR (CDCl₃): δ3.08 t (6 H, ³J$_{HH}$=5.92 Hz, H₂CN$_{ax}$), 2.81 t (6 H, H₂CN$_{eq}$), 1.31 s (3 H, NH). IR (KBr, cm⁻¹): 3428 s, 2104 vs (N≡C stretch). The volatile liquid collected in the cold trap consisted of essentially pure Me₃SiNCS (δ(H) 0.31 ppm).

Preparation of

SCN—Si(NHCH₂CH₂)₃N

When the preparation of 1-(thiocyanato)azasilatrane was attempted with an older, partially decomposed sample of

[H—Si(NH₂CH₂CH₂)(N(SiMe₃)CH₂CH₂)₂N]⁺.SCN⁻

(50% as judged by ¹H NMR spectroscopy), a 2:1 mixture of its —NCS isomer and azasilatrane was isolated. The high-resolution mass spectrum of the mixture is identical, within the experimental error, with that of 1-(thiocyanato)azasilatrane. For the M⁺ peak of the mixture, m/e 229.0820 (calcd 229.08175) was found. By comparison of the 1H NMR spectrum of the mixture with that of pure 1-(thiocyanato)azasilatrane, the following peaks could be assigned to its —NCS isomer: δ3.03 t (6 H, ³J$_{HH}$=5.95 Hz, H₂CN$_{ax}$), 2.78 t (6 H, H₂CN$_{eq}$). IR (KBr, cm⁻¹): 2073 s (C≡N stretch of NCS).

Preparation of

H₂N—Si(NHCH₂CH₂)₃N

In a 100-mL side-arm flask 3.10 g (15.0 mmol) of (chloro)azasilatrane

Cl—Si(NHCH₂CH₂)₃N)

(prepared by the method of D. Gudat et al., *Organometallics*, 8, 2772 (1989), which is incorporated herein by reference) was mixed with 1.17 g of NaNH₂ (30.0 mmol, 100% excess, available from Aldrich ™ Chemical Co.) in a dry box. About 50 mL of liquid NH₃ was condensed into the flask from a sodium/ammonia solution. The solution was kept at −50° C. in a cold ethanol bath and stirred for 1 h. It was then allowed to warm to room temperature with slow evaporation of the NH₃. The residue was extracted with four 15-mL portions of benzene. After removing the solvent, an asphalt-like sticky liquid resulted. Upon distillation at 100°-102° C. and 15 microns of pressure, 0.95 g of colorless product was obtained, which dissolves easily in common organic solvents; mp approximately 35° C. ¹H NMR (C₆D₆):

δ2.78 (t, 6 H, SiNHCH$_2$), 2.14 (t, 6 H, SiNHCH$_2$CH$_2$N), 0.89 (broad, 3 H, NH), 0.095 (broad, 2 H, NH$_2$). $^{13}$C NMR (C$_6$D$_6$): δ50.11 (SiNHCH$_2$), δ37.13 ((CH$_2$)$_3$N). $^1$H NMR (CDCl$_3$): 2.78 (t, 6 H, SiNHCH$_2$), 2.41 (t, 6 H, CH$_2$N). $^{29}$Si (C$_6$D$_6$): δ −72.63 ppm. This complex can be easily protonated to form

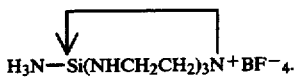

This can be done by adding 85% HBF$_4$.O(C$_2$H$_5$)$_2$ (D=1.15 g/mL) dropwise to a solution of

in C$_6$H$_6$ under argon. A white precipitate forms in almost quantitative yield. This precipitate is slightly soluble in CH$_3$CN; mp 198°-200° C. $^1$H NMR (CD$_3$CN): δ2.98 (t, 6 H, NH$_3$SiNCH$_2$) 2.83 (t, 6 H, (CH$_2$)$_3$N). $^{13}$C NMR (CD$_3$CN): 50.83 (NH$_3$SiNHCH$_2$), 36.511 ((CH$_2$)$_3$N)).

Preparation of

(Chloro)azasilatrane (0.25 g, 1.2 mmol, prepared by the method of D. Gudat et al., *Organometallics*, 8, 2772 (1989), which is incorporated herein by reference) was mixed with 0.1 g of LiNMe$_2$ (1.9 mmol, 58% excess, available from Aldrich ™ Chemical Co.) in a 50 mL flask in a dry box. The addition of 30 mL of diethyl ether led to the formation of a suspension which was stirred overnight and then filtered. After the solvent was removed, a yellowish residue was extracted with four 10-mL portions of benzene. Removing benzene under vacuum afforded 0.103 g (0.48 mmol, 40%) of the product as a white powder. $^1$H NMR (C$_6$D$_6$): δ 2.74 (s, 6 H, N(CH$_3$)$_2$, 2.74 (dr, 6 H, SiNHCH$_2$), 2.08 (t, 6 H, SiNHCH$_2$CH$_2$). $^1$H NMR (CDCl$_3$): 2.99 (t, 6 H, SiNHCH$_2$) 2.41 (s, 6H, N(CH$_3$)$_2$), 2.62 (t, 6 H, SiNHCH$_2$CH$_2$).

Preparation of

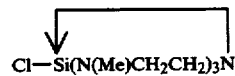

(2.04 g, 9.50 mmol, prepared by the method of D. Gudat et al., *Organometallics*, 8, 2772 (1989), which is incorporated herein by reference) was dissolved in 25 mL of CH$_2$Cl$_2$, to which was added a solution of N-chlorosuccinimide (1.27 g, 9.5 mmol, available from Aldrich Chemical Co.) in 20 mL of CH$_2$Cl$_2$, over a period of 10 min. The solution was stirred for 30 min at room temperature and then the solvent was removed under vacuum. The residue was extracted with four 40-mL portions of benzene. The benzene was removed under vacuum giving 1.33 g (57% yield) of product; mp>135° C., decomposed. MS (EI, 70 eV) for $^{28}$Si and $^{35}$Cl isotopic species: 248 (M$^+$), 213 (M$^+$−Cl), 204 (M$^+$−NMe$_2$) . HRMS: M$^+$ 248.12225 (calcd. 248.12240) . $^1$H NMR (C$_6$D$_6$): δ2.02 (t, 6 H, CH$_2$CH$_2$N, $^3J_{HH}$=6.3 Hz), 2.61 (t, 6 H, CH$_2$CH$_2$N), 3.06 (s, 9 H, SiNCH$_3$, $^3J_{HH}$=4.5 Hz). $^{13}$NMR (C$_6$D$_6$): 67 39.25 (SiNCH$_3$), 46.78 (CH$_2$CHhd 2N), 47.69 (CH$_2$CH$_2$N). $^{29}$Si NMR (CD$_2$Cl$_2$): δ−85.6.

Preparation of

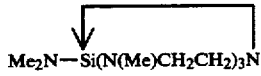

(0.12 g, 0.48 mmol, prepared as described above) in 10 mL of diethyl ether was added dropwise to a suspension of 0.1 g of LiNMe$_2$ (1.96 mmol, 300% excess) in 20 mL of diethyl ether. The solution was stirred for one day at room temperature and then filtered. The ether was removed giving 0.095 g (0.37 mmol, 81% yield) of product. $^1$H NMR (C$_6$D$_6$): δ2.21 (t, 6 H, SiNMeCH$_2$CH$_2$N, $^3J_{HH}$=6.3 Hz) , 2.61 (t, 6 H, SiNMeCH$_2$CH$_2$N) , 2.64 (s, 9 H, SiNCH$_3$) , 2.82 (s, 6 H, N(CH$_3$)$_2$).

Preparation of

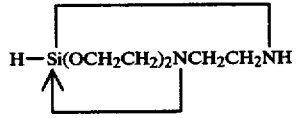

To a solution of HSi(NMe$_2$)$_3$ (8.27 g, 50.7 mmol, available from Huls American Chemical Co. , Bristol, Pa.) dissolved in 50 mL of dry THF in a 100-mL side-arm flask was added the ligand N(CH$_2$CH$_2$OH)$_2$(CH$_2$CH$_2$NH$_2$) (10 mL) at −20° C. Some white precipitate was seen immediately. When the addition was over, the solution was allowed to warm to room temperature. It was then refluxed for 4 h until the evolution of HNMe$_2$ gas ceased. The solvent was removed under vacuum to give 6.3 g of pure crystalline product (72.2% ) , which was sublimed under vacuum at 65° C. The compound dissolves well in organic solvents. $^1$H NMR (C$_6$D$_6$): δ3.58 (t, 4 H, OCH$_2$) , 2.72 (t, 2 H, NHCH$_2$) 2.43 (m, 6 H, (CH$_2$)$_3$N). $^{13}$C NMR (C$_6$D$_6$): δ56.35 (OCH$_2$) , 51.10 (OCH$_2$CH$_2$N) , 50.65 (NHCH$_2$) , 36.23 (NHCH$_2$CH$_2$N).

Preparation of

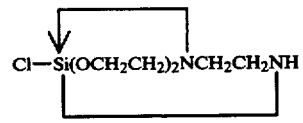

A solution of 0.73 g (4.20 mmol) of

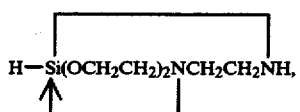

prepared as described above, dissolved in 10 mL of CH$_2$Cl$_2$ was cooled to −50° C. in an ethanol cold bath. A solution of 0.599 g of N-chloro-succinimide (available from Aldrich ™ Chemical Co dissolved in 10 mL of CH$_2$Cl$_2$ was added dropwise, and the mixture allowed to warm to room temperature. It was then stirred for another 30 min. The volatiles were removed under vacuum to give 0.68 g of product (77%), which was purified by extraction of impurities with benzene. The compound can be slowly sublimed at 90° C. under 15.2 Torr without decomposition. $^1$H NMR (CDCl$_3$): δ3.93 (t, 4 H OCH$_2$), 3.06 (t, 2 H, SiNHCH$_2$), 2.93 (m, 6 H, (CH$_2$)$_3$N.

Preparation of

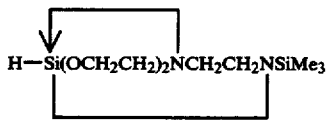

To a 25 mL benzene solution of 1.10 g of

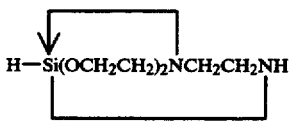

(6.32 mmol), prepared as described above, was added 1.28 g of Et$_3$N (12.6 mmol, available from Aldrich ™ Chemical Co.) and 0.80 mL Me$_3$SiCl (6.32 mmol, available from Aldrich ™ Chemical Co.). The mixture was refluxed overnight and the solid HCl.NEt$_3$ was filtered off. Removal of the volatiles in vacuum afforded 1.462 g of crystalline product (94%) which can be vacuum sublimed at 80° C. at 10$^{-3}$ torr. $^1$H NMR (C$_6$D$_6$): δ 4.96 (s, 1 H, SiH), 3.39 (t, 4 H, OCH$_2$), 2.60 (t, 3 H, Me$_3$SiNCH$_2$), 1.89 (m, 6 H, (CH$_2$)$_3$N), 0.36 (s, 9 H, SiMe$_3$).

Preparation of

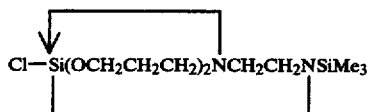

To 0.891 g of

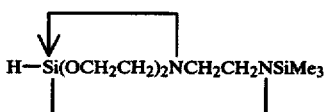

(3.62 mmol) in 25 mL of CH$_2$Cl$_2$ was added 0.484 g of N-chloro-succinimide (3.62 mmol). The solution was stirred for 2 h. The by-product H-succinimide was then extracted with benzene leaving 0.31 g of pure product. $^1$H NMR (CDCl$_3$): δ3.93 (t, 4 H, OCH$_2$), 3.06 (t, 2 H, Me$_3$SiNCH$_2$), 2.91 (m, 6 H, OCH$_2$)$_3$N].

Silicon Type A Compounds

Preparation of

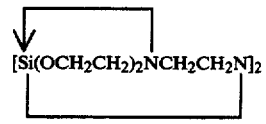

To 30 mL of a THF solution of

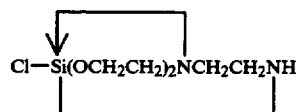

(0.07 g, 0.3 mmol), prepared as described above, was added 0.17 mL of a 2.0 M LiBu solution (0.34 mmol, 20% excess). The solution was stirred for 2 h and then filtered. Removal of the solvents under vacuum resulted in a colorless product. $^1$H NMR (C$_6$D$_6$): 3.84, 3.82, 3.80 (m, 8 H, OCH$_2$), 3.00 (t, 4 H), 2.78, 2.76 (m, 12 H). $^{13}$C NMR (CDCl$_3$): δ57.86, 57.35, 51.81, 51.04. $^{13}$C NMR (C$_6$D$_6$): δ57.80, 57.26, 53.51, 51.60, 50.67, 37.71.

Preparation of

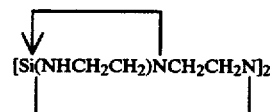

This dimeric species can be prepared in a manner similar to the method used for the preparation of

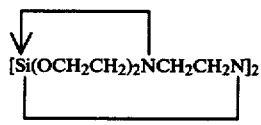

with azasilatrane

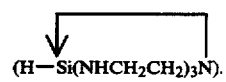

Germanium Type B Compounds

Preparation of

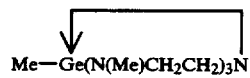

The starting material MeGe(NMe$_2$)$_3$ was prepared by slowly adding dropwise 2.088 g of Me(GeCl$_3$) (10.76 mmol, available from Gelest Inc., Bensalem, Pa.) to 20 mL of a diethyl ether solution of 1.81 g of LiNMe$_2$ (35.5 mmol, 10% excess), which had been previously cooled to −50° C. in an ethanol cold bath. The solution was allowed to warm to room temperature, and then refluxed for 1 h. A solid residue was filtered off and the solvent was removed under vacuum. A pure colorless liquid was obtained by distillation at 80° C. under 15.2 Torr. The yield was 64.7%. $^1$H NMR (C$_6$D$_6$): δ2.59 (s, 18 H) , 0.211 (s, 3 H). $^{13}$C NMR (C$_6$D$_6$): 39.92, −8.49.

The complex

was prepared by introducing MeGe(NMe$_2$)$_3$ (0.26 g, 1.18 mmol) into a 25 mL flask with 0.223 g (1.18 mmol) of Me-Tren and a small particle of (NH$_4$)$_2$SO$_4$ as catalyst. The mixture was heated slowly to 110° C. The reaction was complete as indicated by the cessation of HNMe$_2$ release. Pure product was obtained (0.165 g; 61% yield) by removing unreacted Me-Tren via a sublimation probe. $^1$H NMR (C$_6$D$_6$): δ 2.70 (s, 9 H, 3CH$_3$), 2.66 (t, 6 H, $^3J_{HH}$=6.2 Hz) 2.24 (t, 6 H, (CH$_2$)$_3$N), 0.56 (s, 3 H, GeMe).

Preparation of

The starting material MeGe(NMe$_2$)$_3$ (0.315 g, 1.44 mmol) was mixed with 0.205 g (1.44 mmol) of Tren in a 25-mL side-arm flask. The reaction mixture was heated slowly to 45° C., at which time HNMe$_2$ release with formation of crystalline product was observed. By sublimation, 0.16 g of pure product was collected (48%). $^1$H NMR (C$_6$D$_6$): δ2.77 (t, 6 H, MeGeNHCH$_2$CH$_2$), 2.22 (t, 6 H, MeGeNHCH$_2$CH$_2$), 0.6 (broad, NH), 0.075 (s, 3 H, GeCH$_3$). $^{13}$C NMR (C$_6$D$_6$): δ 52.55 (GeNHCH$_2$), 38.59 ((CH$_2$)$_3$N), 1.37 (GeCH$_3$).

Preparation of

The starting material tetrakis(dimethylamino)germanium (Ge(NMe$_2$)$_4$) was prepared by adding 40 mL of diethyl ether to 2.44 g (47.8 mmol) of Me$_2$NH held at −50° C. in an ethanol cold bath. To this mixture, 2.36 g (11.0 mmol) of GeCl$_4$ (available from Gelest Inc.) was added dropwise. After the addition, the solution was allowed to come to room temperature, stirred overnight, and filtered. The ether was removed under vacuum. A 90% yield of Ge(NMe$_2$)$_4$ was obtained. $^1$H NMR (C$_6$D$_6$): δ2.64 (NCH$_3$).

To 0.696 g (2.8 mmol) of this product was added Me-Tren (0.526 g, 2.8 mmol) and a trace amount of (NH$_4$)SO$_4$ as catalyst. The mixture was heated gradually until no HNMe$_2$ was released. The mixture was distilled carefully and 0.121 g of liquid was obtained (14%). $^1$H NMR (C$_6$D$_6$): 2.97 (s, 6 H, N(CH$_3$)$_2$), 2.73 (s, 9 H, NCH$_3$), 2.66 (t, 6 H, SiNMeCH$_2$), 2.12 (s, 6 H, (CH$_2$)$_3$N).

Aluminum Type A Compounds

Preparation of

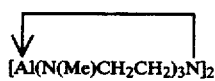

Me-Tren (6.44 g, 34.0 mmol) was added to Ai(NMe$_2$)$_3$ (5.45 g, 34.0 mmol, prepared according to the method of J. K. Ruff, J. Am. Chem. Soc., 83, 2835 (1961), which is incorporated herein by reference). After the reaction was complete, as evidenced by the cessation of the evolution of bubbles of Me$_2$NH, 120 mL of THF was added and the solution was stirred at room temperature for 2 h. After removing the solvent, the product was sublimed at 110° C. at 5×10$^{-3}$ Torr giving a white solid; mp 105° C. The product can also be recrystallized from pentane. Elemental analysis: C, 50.44 (calcd. 50.92) H, 10.05 (calcd. 9.97) N, 25.59 (calcd. 26.39). HRMS: M+ 424.31628 (calcd. 424.31630). $^1$H NMR (C$_6$D$_6$): δ 1.88 (dd, J=4.9, 13.2 Hz, 1 H), 2.12 (dd, J =5.0, 13.1 Hz, 1 H), 2.24 (m, 1 H), 2.31 (m, 1 H), 2.44 (ddd, J=5.1, 13.3, 13.3 Hz), 2.65 (5, 3 H, CH$_3$), 2.67–2.56 (m, 2 H), 2.85–2.78 (m, 2 H) 2.87 (s, 3 H, CH$_3$) 2.91 (s, 3 H, CH$_3$), 2.96 (m, 1 H), 3.04 (m, 1 H), 3.42 (ddd, J=49, 13.1, 13.1 Hz, 1 H). $^{13}$C NMR (C$_6$D$_6$): δ 39.81, 40.75, 41.90 (CH$_3$'s); 52.47, 53.16, 53.56, 53.71, 54.24, 55.98 (CH$_2$'s). $^{27}$Al NMR (C$_6$D$_6$): δ82.5 (Δν$_{\frac{1}{2}}$=130 Hz).

Preparation of

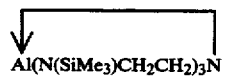

Tris(dimethylamino)aluminum (1.93 g, 12 mmol) and TMS-Tren (4.40 g, 12 mmol) in 170 mL of toluene were stirred and heated to reflux for 20 h. Solvent removal under vacuum afforded a yellowish oil. $^1$H NMR (d$_8$-toluene): δ0.21 (s, 9 H, SiMe$_3$), 2.02 (t, J=5.4 Hz, 2 H), 2.75 (t, J=5.3 Hz, 2 H). $^{13}$C NMR (d$_8$-toluene): δ1.22 (SiMe$_3$), 41.29 (SiNCH$_2$), 58.77 (NCH$_2$).

Boron Type A Compounds

Preparation of

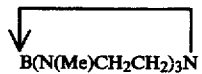

Tris(dimethylamino)boron (2.77 g, 19.4 mmol, available from Aldrich ™ Chemical Co.) was combined with Me-Tren (3.20 g, 17.0 mmol) and a small amount of (NH$_2$)$_2$SO$_4$ as a catalyst in 50 mL of toluene. The mixture was stirred and heated to 90°–95° C. under a reflux condenser for 60 h until gas evolution ceased. A small amount of a white precipitate was filtered off. The solvent was removed from the filtrate and the yellowish residue was sublimed twice at 50° C. under 0.07 Torr; mp 134.5°–135.5° C. HRMS M+: 196.18605 (calc. 196.18593). Elemental analysis: C 55.35 (calc. 55.12), H 10.65 (calc. 10.79), N 28.101 (calc. 28.57). $^1$H NMR (C$_6$D$_6$): δ 2.13 (t, 5.6 Hz, 2 H, NCH$_2$), 2.58 (t broad, J=5.6 Hz, 2 H, CH$_2$NMe) , 2.67 (s, 3 H, CH$_3$N). $^{13}$C NMR (C$_6$D$_6$): δ37.05 (CH$_3$), 52.36 (CH$_2$NMe), 57.07 (N(CH$_2$)$_3$). $^{11}$B NMR (C$_6$D$_6$): δ10.1 (Δν$_{\frac{1}{2}}$=34 Hz).

Preparation of

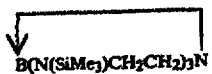

TMS-Tren (3.1 g, 8.5 mmol) was added to 1.6 g (excess) of B(NMe$_2$)$_3$ and a catalytic amount of (NH$_4$)$_2$SO$_4$. The reaction mixture was refluxed for 40 h. After gas evolution ceased, all volatile components were removed under vacuum and the resulting solid was sublimed at 100° C. under 5×10$^{-3}$ Torr. A white sublimate was obtained; mp 85° C. HRMS: M+ 370.25683 (calc. 370.25757). Elemental Analysis: C, 49.74 (calc. 48.62), H 9.91 (calc. 10.61), N 16.49 (calc. 15.12). $^1$H NMR (C$_6$D$_6$): δ0.23 (s, 9 H, Si(CH$_3$)$_3$), 1.72 (ddd, 1 H, J=5.9, 11.5, 11.5 Hz), 2.16 (dd, 1 H, J=3.9, 11.2 Hz), 2.69 (dd, 1 H, J=5.9, 12.2 Hz), 2.82 (ddd, 1 H, J=3.8, 12.2, 12.2 Hz). $^{13}$C NMR (C$_6$D$_6$): δ1.72 (Si(CH$_3$)$_3$), 44.43 (CH$_2$NSiMe$_3$), 60.23 (N(CH$_2$)$_3$). $^{11}$B NMR (C$_6$D$_6$): δ 16.1 (Δν$_{\frac{1}{2}}$=100 Hz).

Tin Type B Compounds

Preparation of

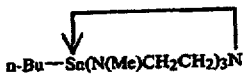

This complex can be prepared from n-BuSn(NMe$_2$)$_3$ and Me-Tren in the following manner. Me-Tren (25.4 g, 135 mmol) and n-butyl-tris(dimethylamino)stannane (41.5 g, 135 mmol, prepared according to the method of K. Jones et al., *J. Chem. Soc.*, 1944 (1965), which is incorporated herein by reference) were stirred in 200 mL of toluene for 4 h. The volatiles were removed under vacuum and the crude product distilled (bp 119-120° C., 0.01 Torr) giving 90% yield of a colorless liquid. Anal. Calcd (found) for C$_{13}$H$_{30}$N$_4$Sn: C, 43.24 (42.72), H, 8.37 (8.48), N, 15.52 (15.72). MS (EI, 70 eV): calcd C$_{13}$H$_{29}$N$_4$$^{120}$Sn (M+−H) 361.14142 (found, 61.14197).

Vanadium Type B Compounds

Preparation of

This complex can be prepared from

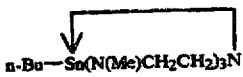

((n-butyl) azastannatrane) and a vanadium alkoxide in the following manner. The vanadium alkoxide OV(O-i-Pr)$_3$ (2.12 g, 8.70 mmol, prepared according to the method of D. M.-T. Chan et al. *Inorg. Chem.*, 25, 4170 (1986), which is incorporated herein by reference) in 50 mL of toluene was combined with an equimolar amount of (n-butyl)azastannatrane. The reaction mixture was heated at 70° C. for 5 h. After the solvent was removed under vacuum, n-BuSn(O—i—Pr)$_3$ was extracted with n-pentane and the solid residue washed twice with the same solvent. Sublimation at 80°-100° C. and 5 mTorr gave a red pure product (80% yield); mp 175° C., decomposed. Analysis Calcd (found) for C$_9$H$_{21}$N$_4$OV: C, 42.86 (41.99) H, 8.39 (8.56) N, 22.21 (21.42). High resolution MS: calcd 252.11550, found 252.11498. FT-IR (KBr, cm$^{-1}$): 962s, ν(V=O)). $^1$H NMR (C$_6$D$_6$): δ4.05 (s, 9H, CH$_3$), 3.02 (unresolved due to $^3$J$_{VH}$, 6 H, V—N—CH$_2$), 2.32 (t, 6 H, V—N—CH$_2$—CH$_2$, $^3$J$_{HH}$=5.7 Hz). $^{13}$C NMR (C$_6$D$_6$, 75.429 MHz): δ60.32 ($^2$J$_{VC}$=7.2 Hz), 55.51 ($^2$J$_{VC}$=4.5 Hz), 51.50 ($^2$J$_{VC}$=2.4 Hz).

An x-ray crystal structure of this vanadium complex was carried out. The complex displays an essentially trigonal planar geometry around the pseudoequatorial nitrogens with the planes coparallel with the (O—V axis and puckered five-membered rings in a "paddle-wheel" arrangement.

Preparation of

This can be prepared in a manner similar to

using the vanadium alkoxide t-Bu—N=V(O—i—Pr)$_3$, prepared analogous to the method of preparation of p-tolyl—N=V(O—t—u)$_3$ of D. D. Devore et al., *J. Am. Chem. Soc.*, 109, 7408 (1987), which is incorporated herein by reference. In general, VOCl$_3$ was combined with t-butyl-isocyanate octane and refluxed. The product t-Bu—N=VCl$_3$ was isolated and combined with KO—i—Pr in THF to form t-Bu—N=V(O—i—Pr)$_3$.

Molybdenum Type B Compounds

Preparation of

This complex can be prepared from

and a molybdenum alkoxide in the following manner. The molybdenum alkoxide N≡Mo(O—t—Bu)$_3$ (0.35 g, 1.1 mmol, prepared according to the method of D. M.-T. Chan et al. *Inorg. Chem.*, 25, 4170 (1986), which is incorporated herein by reference) in 50 mL of toluene was combined with an equimolar amount of (n-butyl)azastannatrane. The reaction mixture was heated at 70° C. for 5 h. After the solvent was removed under vacuum, the n-BuSn(O—t—Bu)$_3$ was extracted with n-pentane and the solid residue washed twice with the same solvent. Sublimation at 80°-100° C. and 5 mTorr gave a yellow pure product (70% yield); mp 130° C., decomposed. Anal. Calcd (found) for C$_9$H$_{21}$N$_5$Mo: C, 36.61 (36.83) H, 7.17 (7.47) N, 23.72 (22.90). High resolution MS: calcd 291.08600, found 291.08662. FT-IR (K Br, cm$^{-1}$): 991s, ν(Mo≡N)). $^1$H NMR (C$_6$D$_6$): δ4.09 (s, 9 H, CH$_3$), 2.86 (t, 6 H, Mo—N—CH$_2$, $^3$J$_{HH}$=5.6 HZ), 2.11 (t, 6 H, MO—N—CH$_2$—CH$_2$, $^3J_{HH}$=5.6 HZ). $^1$H NMR (C$_6$D$_6$): δ58.87, 58.44, 49.98.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of the formula

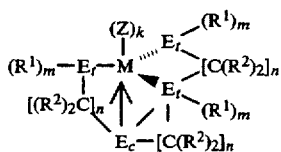

wherein:
(a) M is selected from the group consisting of a lanthanide, an actinide, a Group IIIA metal, a Group IIIA metalloid, a Group IVA metal, a Group IVA metalloid, a Group VA metal, a Group VA metalloid, a Group IIIB metal, a Group IVB metal, a Group VB metal, a Group VIB metal, a Group VIIB metal, and a Group VIIIB metal;
(b) k=0–1;
(c) Z is a nitrogen-bound, silicon-bound, or sulfur-bound ligand;
(d) E$_c$ and each E$_t$ are independently selected from the group consisting of N, P, and As;
(e) m=1;
(f) each R$^1$ is independently selected from the group consisting of hydrogen, (C$_2$-C$_{20}$)alkyl, (C$_2$-C$_{20}$)alkenyl, (C$_2$-C$_{20}$)alkynyl, (C$_6$-C$_{18}$)aryl, (C$_7$-C$_{20}$)aralkyl, a (C$_5$-C$_{18}$)heterocycle, and triorganosilyl;
(g) n=1–4; and
(h) each R$^2$ is independently selected from the group consisting of hydrogen, (C$_1$-C$_{20}$)alkyl, (C$_2$-C$_{20}$)alkenyl, (C$_2$-C$_{20}$)alkynyl, (C$_6$-C$_{18}$)aryl, (C$_7$-C$_{20}$)aralkyl, and a (C$_5$-C$_{18}$)heterocycle.

2. The compound of claim 1 wherein k=0 and M is selected from the group consisting of B, Al, Ga, In, Tl, Ge, Si, Sn, Ti, Zr, Hf, V, Nb, Ta, Cr, Mo, W, Mn, Tc, Re, Fe, Ru, Os, Co, Rh, and Ir.

3. The compound of claim 2 wherein a molecule of the compound is bound to another molecule of the compound through two E$_t$—M bonds to form a dimeric species.

4. The compound of claim 1 wherein k=1 and M is selected from the group consisting of Si, Ge, Sn, Ti, Zr, Hf, V, Nb, Ta, Cr, Mo, and W.

5. The compound of claim 4 wherein a molecule of the compound is bound to another molecule of the compound through two E$_t$—M bonds to form a dimeric species.

6. The compound of claim 4 wherein Z is selected from the group consisting of —NH$_2$, —N(CH$_3$)$_2$, —NCS, and —N$_3$.

7. The compound of claim 4 wherein E$_c$=E$_t$=N.

8. A compound of the formula

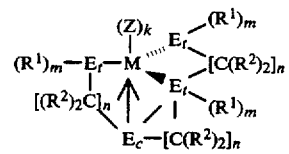

wherein:
(a) M is selected from the group consisting of a Group IVA metal, a Group IVA metalloid, a Group IVB metal, a Group VB metal, and a Group VIB metal;
(b) k=0–1;
(c) Z is a nitrogen-bound, silicon-bound, or sulfur-bound ligand;
(d) E$_c$ is selected from the group consisting of N, P, and As;
(e) each E$_t$ is independently selected from the group consisting of N, P, As, and m=1;
(f) each R$^1$ is independently selected from the group consisting of hydrogen, (C$_1$-C$_{20}$)alkyl, (C$_2$-C$_{20}$)alkenyl, (C$_2$-C$_{20}$)alkynyl, (C$_6$-C$_{18}$)aryl, (C$_7$-C$_{20}$)aralkyl, a (C$_5$-C$_{18}$)heterocycle, and triorganosilyl;
(g) n=1–4; and
(h) each R$^2$ is independently selected from the group consisting of hydrogen, (C$_1$-C$_{20}$)alkyl, (C$_2$-C$_{20}$)alkenyl, (C$_2$-C$_{20}$)alkynyl, (C$_6$-C$_{18}$)aryl, (C$_7$-C$_{20}$)aralkyl, and a (C$_5$-C$_{18}$)heterocycle.

9. The compound of claim 8 wherein each E$_t$ is independently selected from the group consisting of N, P, and As, and each R$^1$ is independently selected from the group consisting of hydrogen, (C$_1$-C$_4$)alkyl, and triorganosilyl.

10. The compound of claim 8 wherein n=2 and each R$^2$ in —[C(R$^2$)$_2$]$_n$— is hydrogen.

11. A compound of the formula

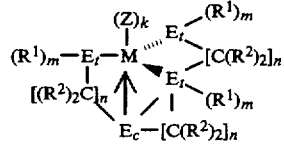

wherein:
(a) M is selected from the group consisting of a lanthanide, an actinide, a Group IIIA metal, a Group IIIA metalloid, a Group IVA metal, a Group IVA metalloid, a Group VA metal, a Group VA metalloid, a Group IIIB metal, a Group IVB metal, a Group VB metal, a Group VIB metal, a Group VIIB metal, and a Group VIIIB metal;
(b) k=0–1;
(c) Z is selected from the group consisting of hydrogen, halide, and a ligand which bonds to M through N, O, P, S, As, Si, or C;
(d) E$_c$ is N;
(e) each E$_t$ is N or O, wherein at least one E$_t$ is N and at least one E$_t$ is O, with the proviso that
  (i) when E$_t$ is N, m=1; and
  (ii) when E$_t$ is O, m=0;
(f) each R$^1$ is independently selected from the group consisting of hydrogen, (C$_1$-C$_{20}$)alkyl, (C$_2$-C$_{20}$)alkenyl, (C$_2$-C$_{20}$)alkynyl, (C$_6$-C$_{18}$)aryl, (C$_7$-C$_{20}$ 0)aralkyl, a ($C_5$-$C_{18}$)heterocycle, and triorganosilyl;

(g) n=1–4; and (h) each $R^2$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, and a ($C_5$-$C_{18}$)heterocycle.

12. The compound of claim 11 wherein a molecule of the compound combines with another molecule of the compound through two $E_t$—M bonds to form a dimeric species.

13. A compound of the formula

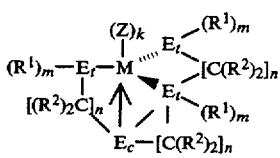

wherein:

(a) M is selected from the group consisting of a Group IVB metal, a Group VB metal, a Group VIB metal, a Group VIIB metal, a Group VIIIB iron group metal, and a Group VIIIB cobalt group metal;

(b) k=0–1;

(c) Z is selected from the group consisting of hydrogen, halide, and a ligand which bonds to M through N, O, P, S, As, Si, or C;

(d) $E_c$=$E_t$=N;

(e) m=1;

(f) each $R^1$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, a ($C_5$-$C_{18}$)heterocycle, and a triorganosilyl;

(g) n=1–4; and (h) each $R^2$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, and a ($C_5$-$C_{18}$)heterocycle.

14. The compound of claim 13 wherein "M—Z" is V=O.

15. The compound of claim 13 wherein "M—Z" is V=$NR^7$ wherein $R^7$ is selected from the group consisting of ($C_1$-$C_4$)alkyl and triorganosilyl.

16. The compound of claim 13 wherein "M-Z" is Mo≡N.

17. A compound of the formula

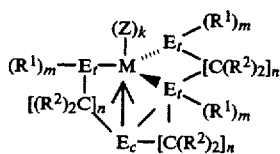

wherein:

(a) M is selected from the group consisting of Ge and Sn;

(b) k=0–1;

(c) Z is selected from the group consisting of hydrogen, halide, and a ligand which bonds to M through N, O, P, S, As, Si, or C;

(d) $E_c$=$E_t$=N;

(e) m=1;

(f) each $R^1$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, a ($C_5$-$C_{18}$heterocycle, and triorganosilyl;

(g) n=1–4; and (h) each $R^2$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_7$-$C_{20}$)aralkyl, and a ($C_5$-$C_{18}$)heterocycle.

18. A compound of the formula

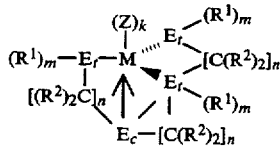

wherein:

(a) M is Ti;

(b) k=1;

(c) Z is selected from the group consisting of:
  (i) —N($R^5$)$_2$ wherein each $R^5$ is independently selected from the group consisting of hydrogen and ($C_1$-$C_4$)alkyl; and
  (ii) —$SR^6$ wherein $R^6$ is selected from the group consisting of ($C_1$-$C_{10}$)alkyl, ($C_2$-$C_{10}$)alkenyl, ($C_6$-$C_{18}$)aryl, and ($C_7$-$C_{20}$)aralkyl;

(d) $E_c$ is N;

(e) each $E_t$ is O, and m=0;

(f) n=1–4; and (g) each $R^2$ is independently selected from the group consisting of hydrogen, ($C_1$-$C_{20}$)alkyl, ($C_2$-$C_{20}$)alkenyl, ($C_2$-$C_{20}$)alkynyl, ($C_6$-$C_{18}$)aryl, ($C_6$-$C_{20}$)aralkyl, and a ($C_5$-$C_{18}$)heterocycle.

19. The compound of claim 18 wherein a molecule of the compound is combined with another molecule of the compound through two $E_t$—M bonds to form a dimeric species.

* * * * *

UNITED STATES PATENT AND TRADEMARK OFFICE
CERTIFICATE OF CORRECTION

PATENT NO. : 5,344,948
DATED : September 6, 1994
INVENTOR(S) : John G. Verkade

It is certified that error appears in the above-indentified patent and that said Letters Patent is hereby corrected as shown below:

Col. 4, line 14, delete "($C_2$-$C_{18}$) alkynyl," and insert --($C_2$-$C_{20}$) alkynyl,--;
Col. 4, line 35, delete "Pt," and insert --Pr,--;
Col. 8, line 42, delete ""R"" and insert --"$R^2$"--;
Col. 8, line 43, delete "-($CH^2$)-" and insert -- -$(CH_2)_p$- --;
Col. 16, line 56, delete "IV" and insert --IVA--;
Col. 17, line 1, delete "    " and insert -- -$SiR_3$ --;
Col. 20, line 40, delete "10 Torr" and insert --$10^{-9}$ Torr--;
Col. 21, line 21, delete ""$E_t$"" and insert --"$E_c$"--;
Col. 22, line 49, delete "Tort" and insert --Torr--;
Col. 23, line 35, delete "($CH_{b2}O$)" and insert --($CH_2O$)--;
Col. 25, line 32, delete "3.42-352" and insert --3.42-3.52--;
Col. 31, line 45, delete "dr" and insert --dt--;
Col. 32, line 9, delete "$^{13}$NMR" and insert --$^{13}$C NMR--;
Col. 32, line 9, delete "67 39.25" and insert --δ 39.25--;
Col. 32, line 10, delete "($CH_2$CHhd 2N)" and insert --($CH_2CH_2N$)--;
Col. 35, line 60, delete "($NH_4$)$SO_4$" and insert --$(NH_4)_2SO_4$--;
Col. 37, line 42, delete "61.14197" and insert --361.14197--;
Col. 38, line 31, delete "N=V(O-t-u)$_3$" and insert --N=V(O-t-Bu)$_3$--;
Col. 39, line 38, delete "($C_2$-$C_{20}$)alkyl" and insert --($C_1$-$C_{20}$)alkyl--;
Col. 42, line 21, delete "($C_5$-$C_{18}$heterocycle" and insert --($C_5$-$C_{18}$)heterocycle--; and

UNITED STATES PATENT AND TRADEMARK OFFICE
CERTIFICATE OF CORRECTION

PATENT NO. : 5,344,948
DATED : September 6, 1994
INVENTOR(S) : John G. Verkade

It is certified that error appears in the above-indentified patent and that said Letters Patent is hereby corrected as shown below:

Col. 42, lines 50-51, delete "$(C_6-C_{20})$aralkyl" and insert --$(C_7-C_{20})$aralkyl--.

Signed and Sealed this

Fourth Day of August, 1998

Attest:

Attesting Officer

BRUCE LEHMAN

Commissioner of Patents and Trademarks